United States Patent [19]
Bigge et al.

[11] Patent Number: 6,057,313
[45] Date of Patent: May 2, 2000

[54] GLUTAMATE (AMPA/KAINATE) RECEPTOR ANTAGONISTS: N-SUBSTITUTED FUSED AZACYCLOALKYLQUINOXALINEDIONES

[75] Inventors: Christopher Franklin Bigge, Ann Arbor; Thomas Charles Malone, Canton; Robert Michael Schelkun, Ypsilanti; Chung Stephen Yi, Ann Arbor, all of Mich.

[73] Assignee: Warner-Lambert Company, Morris Plains, N.J.

[21] Appl. No.: 08/869,515

[22] Filed: Jun. 5, 1997

Related U.S. Application Data

[63] Continuation of application No. 08/404,400, Mar. 14, 1995, abandoned.

[51] Int. Cl.$^7$ ............... A61K 31/495; C07D 471/04; C07D 487/04; C07D 217/04
[52] U.S. Cl. ............ 514/215; 540/578; 514/250; 544/345; 546/143
[58] Field of Search ............ 544/345; 514/250, 514/215; 540/578

[56] References Cited

U.S. PATENT DOCUMENTS

| | | | |
|---|---|---|---|
| 4,889,855 | 12/1989 | Jacobsen et al. | 514/250 |
| 5,081,123 | 1/1992 | Honoré et al. | 514/250 |
| 5,308,845 | 5/1994 | Honoré et al. | 514/250 |

FOREIGN PATENT DOCUMENTS

| | | | |
|---|---|---|---|
| 488959 | 6/1992 | European Pat. Off. | |
| 94-09000 | 4/1994 | WIPO | 544/345 |
| 94-26747 | 11/1994 | WIPO | 544/345 |

OTHER PUBLICATIONS

Advanced Organic Chemistry, Second Edition, Carey et al, Plenum Press, pp. 493–497, 1984.
M. A. Rogawski, TiPS 14, 325 (1993).
H. Li and A.M. Buchan, J. Cerebr. Blood Flow Metab. 13, 933 (1993).

(List continued on next page.)

*Primary Examiner*—Mark L Berch
*Attorney, Agent, or Firm*—Elizabeth M. Anderson

[57] ABSTRACT

Novel N-substituted azacycloalkyl ring fused 2,3-quinoxalinediones are disclosed represented by the formula:

(I)

or a pharmaceutically acceptable salt thereof, wherein $R^1$ is hydrogen, alkyl or W-alkyl; X and Y are independently hydrogen, halogen, nitro, cyano, trifluoromethyl, $SO_2CF_3$, $SO_2R^4$, $SO_2NR^4R^5$, alkyl, alkenyl, $(CH_2)_zCONR^4R^5$, $(CH_2)_zCOOR^4$, or $NHCOR^4$, wherein $R^4$ and $R^5$ are independently hydrogen, alkyl having 1 to 6 carbon atoms, cycloalkyl or W-alkyl, and z is an integer from 0 to 4; $R^2$ is benzoyl, W, W-alkyl, COcycloalkyl, COalkyl-W, $CONR^3$alkyl, $CONR^3$-W, $CONR^3$alkyl-W, $CSNR^3$alkyl, $CSNR^3$alkyl-W, or a moiety derived from a common amino acid by removal of the —OH from the carboxyl group which is alpha to the amino, wherein —W is aryl, heteroaryl, or the heterocycles piperidinyl, piperazinyl, morpholinyl or pyrrolidinyl, wherein $R^3$ is hydrogen, alkyl or W-alkyl; and m and n are independently 0, 1 or 2 provided that m+n is >1; provided that when $R^2$ is benzoyl, or
X is nitro, Y and $R^1$ are H, m is 2 and n is 1;
when $R^2$ is X is nitro, Y and $R^1$ are H and m is 2 and n is 1; or when $R^2$ is X is bromo, Y and $R^1$ are H, m is 1 and n is 2. The novel N-substituted azacycloalkyl ring fused 2,3-quinoxalinediones may be used, for example, as neuroprotective agents, for treatment of chronic neurodegenerative disorders, as anticonvulsants and in the treatment of schizophrenia, epilepsy, anxiety, pain and drug addiction.

10 Claims, No Drawings

OTHER PUBLICATIONS

B. Nellgard and T. Wieloch, J. Cerebr. Blood Flow Metab. 12, 2 (1992).
R. Bullock et al., J. Cerebr. Blood Flow Metab. 14, 466 (1994).
D. Xue et al., J. Cerebr. Blood Flow Metab. 14, 251 (1994).
X.–J. Xu et al., J. Pharmacol. Exp. Ther. 267, 140 (1993).
T. Namba et al., Brain Res. 638, 36 (1994).
S. E. Browne and J. McCulloch, Brain Res. 641, 10 (1994).
S.I. Yamaguchi et al., Epilepsy Res. 15, 179 (1993).
S.E. Smith et al., Eur. J. Pharmacol. 201, 179 (1991).
T. Klockgether et al., Ann Neurol. 34 (4), 585–593 (1993).
P.T. Francis et al., J. Neurochem. 60 (5), 1589–1604 (1993).
S. Lipton, TINS 16 (12), 527–532 (1993).
S. Lipton et al., New Eng. J. Med. 330 (9), 613–622 (1994).
C.F. Bigge, Biochem Pharmacol. 45, 1547–1561 (1993).
A.M. Buchan et al., Neurosci. Lett (Ireland) 132 (2), 255–8 (1991).
L. Dalgaard et al., Drug Metabolism and Disposition 22 (2), 289–93 (1994).
K. Lippert et al., Eur. J. Pharmacol. 253 (3), 207–13 (1994).
W. Loescher et al., Eur. J. Neurosci. 5(11), 1545–50 (1993).
J. Mosinger et al., Exp. Neurol. 113, 10–17 (1991).
C.F. Bigge and T.C. Malone, Curr. Opin. Ther. Pat., 951 (1993).
C. F. Bigge, et al., *J Med Chem*, 1995, 38, 3720–3740.
"Drug Evaluations Annual, 1993" (A.M.A). pp. 259, 260, 432, 2127.

GLUTAMATE (AMPA/KAINATE) RECEPTOR ANTAGONISTS: N-SUBSTITUTED FUSED AZACYCLOALKYLQUINOXALINEDIONES

This application is a continuation of application Ser. No. 08/404,400, filed Mar. 14, 1995, now abandoned.

BACKGROUND OF THE INVENTION

1. Field of the Invention

This invention is related to 2,3-quinoxalinediones having a N-substituted azacycloalkyl ring fused with the quinoxaline system. The N-substituted azacycloalkyl ring fused 2,3-quinoxalinediones are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates to the use of those quinoxalinediones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as to treat chronic neurodegenerative disorders such as lathyrism, Alzheimer's Disease, Parkinsonism and Huntington's Disease and as anticonvulsants. The compounds of the present invention may also be useful in the treatment of schizophrenia, epilepsy, anxiety, pain and drug addiction.

2. Related Background Art

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Several classes of quinoxalinedione derivatives have been disclosed as glutamate (EAA) receptor antagonists. For example, U.S. Pat. No. 4,889,855, generically discloses compounds of the formulae:

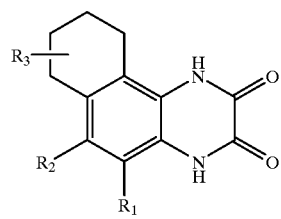

-continued

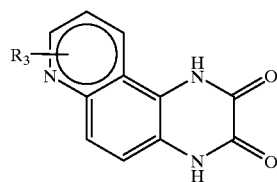

wherein $R_1$, $R_2$ and $R_3$ are independently H, halogen, CN, $NH_2$, $NO_2$, $SO_3H$, $SO_2NH_2$, and $CONH_2$. This reference specifically discloses 6-amino, 6-cyano, 5-carbamoyl, 6-nitro and 5,6-dinitro-7,8,9,10-tetrahydro-2,3-dihydroxybenzo(f)quinoxalines. The reference, however, does not disclose any compounds with an azacycloalkyl fused ring, let alone an N-substituted ring. Nor does the reference disclose or suggest any methods which would allow the preparation of N-substituted azacycloalkyl ring fused compounds. U.S. Pat. No. 5,081,123 and U.S. Pat. No. 5,308,845, describe similar structures except that there is respectively a hydroxy or alkoxy function at the nitrogen on the quinoxalinedione skeleton. Again, however, these references do not suggest or illustrate any examples of N-substituted fused azacycloalkylquinoxalinediones.

Having both NMDA and non-NMDA antagonist properties in a single entity may provide a superior pharmacological profile. Combinations of NMDA and non-NMDA receptor antagonists have shown synergistic activity in focal and global ischemia [K. Lippert, M. Welsch and J. Krieglstein, Eur. J. Pharmacol. 253 (3), 207–13 (1994)], as anticonvulsants [W. Loescher, C. Rundfelt, D. Hoenack, Eur. J. Neurosci. 5 (11), 1545–50 (1993)], and in protection of neuronal degeneration in retina [J. Mosinger, M. Price, H. Bai, H. Xiao, D. Wozniak and J. Olney, Exp. Neurol. 113, 10–17 (1991).

Among excitatory amino acid receptor antagonists recognized for usefulness in the treatment of disorders are those that block AMPA receptors [C. F. Bigge and T. C. Malone, Curr. Opin. Ther. Pat., 951 (1993); M. A. Rogawski, TiPS 14, 325 (1993)]. AMPA receptor antagonists have prevented neuronal injury in several models of global cerebral ischemia [H. Li and A. M. Buchan, J. Cerebr. Blood Flow Metab. 13, 933 (1993); B. Nellgard and T. Wieloch, J. Cerebr. Blood Flow Metab. 12, 2 (1992)] and focal cerebral ischemia [R. Bullock, D. I. Graham, S. Swanson, J. McCulloch, J. Cerebr. Blood Flow Metab. 14, 466 (1994); D. Xue, Z. -G. Huang, K. Barnes, H. J. Lesiuk, K. E. Smith, A. M. Buchan, J. Cerebr. Blood Flow Metab. 14, 251 (1994)]. AMPA antagonists have also shown efficacy in models for analgesia [X. -J. Xu, J. -X Hao, A. Seiger, Z. Wiesenfeld-Hallin, J. Pharmacol. Exp. Ther. 267, 140 (1993)], and epilepsy [T. Namba, K. Morimoto, K. Sato, N. Yamada, S. Kuroda, Brain Res. 638, 36 (1994); S. E. Brown, J. McCulloch, Brain Res. 641, 10 (1994); S. I. Yamaguchi, S. D. Donevan, M. A. Rogawski, Epilepsy Res. 15, 179 (1993); S. E. Smith, N. Durmuller, B. S. Meldrum, Eur. J. Pharmacol. 201, 179 (1991)]. AMPA receptor antagonists have also demonstrated promise in chronic neurodegenerative disorders such as Parkinsonism. [T. Klockgether, L. Turski, T. Honoré, Z. Zhang, D. M. Gash, R. Kurlan, J. T. Greenamyre, Ann. Neurol., 34(4), 585–593 (1993)].

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

Copending U.S. patent application Ser. No. 08/124,770 discloses glutamate receptor antagonist quinoxalinedione derivatives represented by the formula:

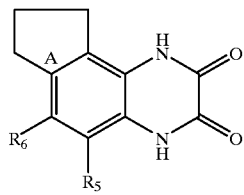

wherein A is a 5 to 7 atom containing ring having a nitrogen which may be substituted by hydrogen, alkyl or $CH_2CH_2OH$. This application does not disclose or suggest compounds having different nitrogen substituents, or the requisite methodology to prepare the same.

An object of this invention is to provide novel N-substituted azacycloalkyl ring fused 2,3-quinoxalinediones which function as either or both NDMA antagonists or non-NMDA antagonists.

A further object of this invention is to provide a pharmaceutical composition containing an effective amount of the N-substituted azacycloalkyl ring fused 2,3-quinoxalinediones to treat cerebrovascular disorders responsive to blocking any or all of NMDA receptors, AMPA receptors and kainate-receptors.

Another object of this invention is to provide a method of treating disorders responsive to the antagonism of glutamate or aspartate receptors in a human by administering a pharmaceutically effective amount of the N-substituted azacycloalkyl ring fused 2,3-quinoxalinediones of this invention.

Another object of this invention is to provide novel methods of preparing N-substituted azacycloalkyl ring fused 2,3-quinoxalinediones.

A further object of this invention is directed to novel intermediates of the N-substituted azacycloalkyl ring fused 2,3-quinoxalinediones of this invention.

SUMMARY OF THE INVENTION

The present invention is directed to compounds represented by the formula (I):

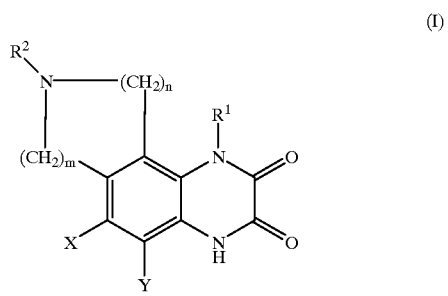

or a pharmaceutically acceptable salt thereof wherein
$R^1$ is hydrogen, an alkyl or an W-alkyl;
X and Y are independently hydrogen, halogen, nitro, cyano, trifluoromethyl, COOH, $CONR^4R^5$, $SO_2CF_3$, $SO_2R^4$ $SONR^4R^5$, alkyl, alkenyl, $(CH_2)_zCONR^4R^5$, $(CH_2)_zCOOR^4$, or $NHCOR^4$, wherein $R^4$ and $R^5$ are independently hydrogen, alkyl having 1 to 6 carbon atoms, cycloalkyl or W-alkyl, and z is an integer from 0 to 4;
W-alkylCOOR$^3$, alkylamine, alkylguanidine, W-aryl, COalkyl, COalkyl-W, CONR$^3$alkyl, CONR$^3$-W, CONR$^3$alkyl-W, CSNR$^3$alkyl, CSNR$^3$alkyl-W or a common amino acid moiety joined by an amide bond, wherein $R^3$ is H, alkyl or W-alkyl; and
m and n are independently 0, 1 or 2 provided that m+n is >1.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate. Alternatively, pharmaceutically acceptable inorganic and organic base addition salts may be used such as sodium hydroxide, potassium hydroxide, lithium hydroxide and the like.

Halogen is fluorine, chlorine, bromine, or iodine; fluorine, chlorine, and bromine are preferred groups.

Alkyl means a straight chained or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Alkenyl means a straight chained or branched chain alkenyl group of two to six carbon atoms or a cyclic alkenyl group of three to seven carbon atoms, for example, but not limited to ethylene, 1,2- or 2,3-propylene, 1-2, 2,3-, or 3,4-butylene, cyclopentene, or cyclohexene.

The letter "W" represents a monocyclic or bicyclic aromatic carbocyclic moiety, which can be substituted or unsubstituted, for example, but not limited to phenyl or naphthyl, or represents a heteroaryl moiety, including for example, thienyl, furyl, tetrazolyl, pyrrolyl, pyrimidinyl, triazolyl and imidazolyl. W also represents the non-aromatic heterocyclic moieties piperidyl, piperazinyl, morpholinyl or pyrrolinyl.

The term "W-alkyl" represents a substituent containing alkyl and W moieties, as defined above; for example, but not limited to benzyl, 2-phenylethyl and 3-phenylpropyl. A preferred W-alkyl substituent is benzyl.

Common amino acid moiety means the naturally occurring α-amino acids, and their enantiomers.

The instant invention is also related to a pharmaceutical composition containing the compound defined by formula I in an amount effective to treat cerebrovascular disorders responsive to the blockade of glutamate receptors, including either or both NMDA receptors and non-NMDA receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism and Alzheimer's disease. The pharmaceutical composition of this invention may also be employed as an analgesic or the treatment of epilepsy.

The invention further relates to a method of treating cerebrovascular disorders responsive to antagonism of glutamate receptors including either or both NMDA receptors and non-NMDA receptors by administering a compound of above-defined formula I in a unit dosage form.

The invention is also related to a method for preparing the compound of formula (I) comprising the steps of:

(a)(i) hydrogenating and acetylating an aromatic nitro group of a compound of formula

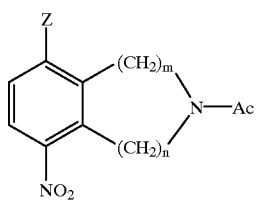

wherein m and n is 0, 1 or 2 and Z is a halogen, or (ii) halogenating a compound of formula

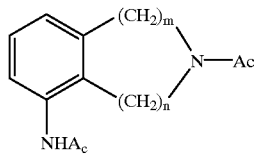

wherein m and n are as previously described, to form a compound of formula

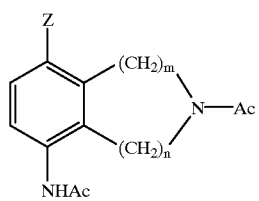

(b) nitrating the compound formed in step (a) to produce a compound of formula

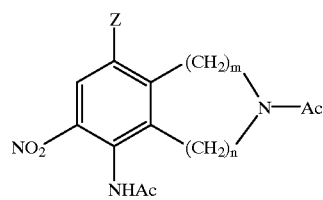

(c) deacetylating the compound of step (b) to produce a compound of formula

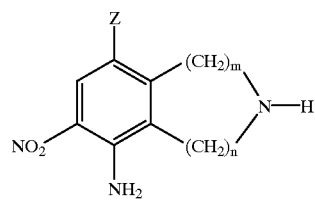

(d) treating the compound of step (c) by either (i) reaction with $R^2X^3$ wherein $R^2$ is the same as defined for formula (I) and $X^3$ is a leaving group, or alternatively reaction with an $R^{2'}CHO$ or $R^{2'}COR^{2''}$ in the presence of a reducing agent, such as, for example, sodium cyanoborohydride in a solvent such as methanol or tetrahydrofuran, wherein $R^{2'}$ and $R^{2''}$ are the same as $R^2$, to produce a compound of formula

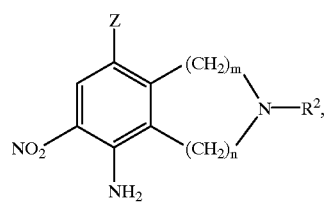

(ii) a non-dehalogenating hydrogenation to produce a compound of formula

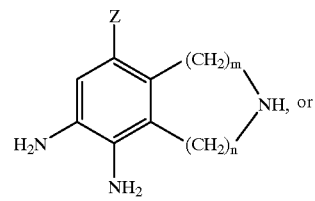

(iii) a dehalogenating hydrogenation to produce a compound of formula

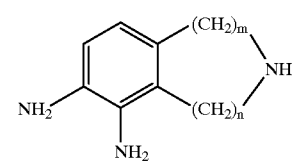

(e) if the compound of step (d)(i) is produced, treating that compound by either (i) a non-dehalogenating hydrogenation to produce a compound of formula

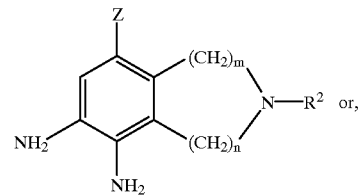

(ii) a dehalogenating hydrogenation to produce a compound of formula

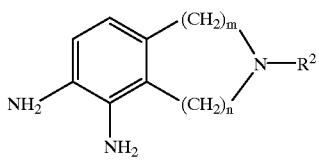

(f) condensation of the compound of any of steps (d)(ii), (d)(iii), (e)(i) or (e)(ii) with oxalic acid or an oxalic acid ester to produce a compound of formula

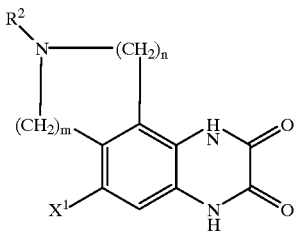

wherein $R^8$ is the same as defined for formula (II), infra, and $X^1$ is hydrogen or halogen, (g) optionally reacting the compound of step (f) with an aromatic electrophillic substituent to produce a compound of formula

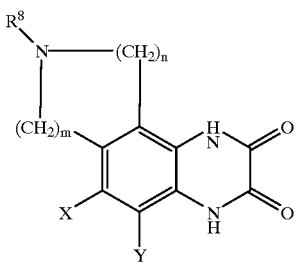

wherein X and Y are the same as defined for formula (I), (h) optionally reacting the compound of steps (f) or (g) wherein $R^8$ is hydrogen with $R^2X^3$ wherein $R^2$ and $X^3$ are as previously described, or alternatively with $R^{2'}CHO$ or $R^{2'}COR^{2''}$ in the presence of a reducing agent, such as, for example, sodium cyanoborohydride in a solvent such as methanol or tetrahydrofuran wherein $R^{2'}$ and $R^{2''}$ are the same as $R^2$, to produce a compound of formula

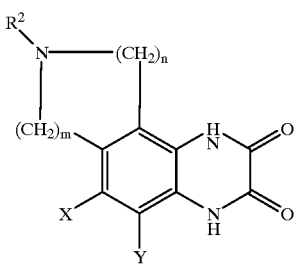

wherein X and Y are as previously described with the exception that if the compound of step (f) wherein $R^8$ is hydrogen is reacted then X is $X^1$ and Y is hydrogen, (i) optionally reacting the compound of step (h) wherein X is $X^1$ and Y is hydrogen with an aromatic electrophillic substituent to produce a compound of formula

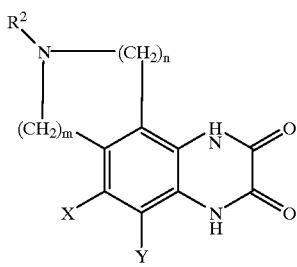

wherein X and Y are as described for the compound of formula (I).

The steps of hydrogenating in the process of this invention may be conducted by a non-dehalogenating hydrogenation, i.e., a relatively mild hydrogenation, and a dehalogenating hydrogenation, i.e., a more powerful hydrogenation. Typically, a non-dehalogenating hydrogenation may be conducted using deactivated Raney nickel catalyst in a hydrogen atmosphere (e.g., 1 atm to 100 psi) in a solvent such as methanol, ethanol, tetrahydrofuran or the like. On the other hand, a dehalogenating hydrogenation can be accomplished, for example, using a palladium-carbon catalyst (Pd/C) under similar conditions or by using any other hydrogenation catalyst that achieves the desired result.

Acetylation is generally accomplished using an acetylating reagent such as acetic anhydride, formic anhydride or a mixed anhydride, either neat or in a solvent. Alternatively, an acid chloride or other activated ester may be employed. Exemplarary solvents include chloroform, dichloromethane, tetrahydrofuran, pyridine and the like. The acetylation is typically conducted at room temperature under a nitrogen or ambient atmosphere.

Typically the halogenating agent employed in the method of this invention is selected from the group consisting of bromine, N-bromosuccinimide, chlorine, and iodochloride or the like. When a brominating agent is employed it is preferably present in an acetic acid/sodium acetate solution or acetic acid/trifluoroacetic acid solution. The halogenation step is generally carried out at a temperature of about 15–50° C. for about 15 minutes to 24 hours.

Either fuming nitric acid or potassium nitrate in an acid selected from the group consisting of trifluoroacetic acid, acetic acid, concentrated sulfuric acid or the like are generally employed during the steps of nitrating in the methods described herein. More particularly, fuming nitric acid in trifluoracetic acid, acetic acid or the like is employed at about 0° C. to room temperature for about 15 minutes to about 8 hours. Alternatively, fuming nitric acid, potassium nitrate or the like in concentrated sulfuric acid may be used.

Deacetylation is generally achieved by contacting the intermediates of this process with a strong acid. For example, 3N HCl can be employed with refluxing for several hours to deacetylate the appropriate intermediate.

The step of condensation in the method of this invention is generally accomplished with oxalic acid or an oxalic acid ester such as dimethyl oxalate or the like. The condensation reaction is preferably carried out at a temperature of about 25–150° C. for about 30 minutes to 24 hours in an aqueous acidic media or an organic solvent such as acetonitrile, methanol or the like.

This invention is further directed to novel intermediates which may be prepared during the preparation of the N-substituted azacycloalkyl ring fused quinoxalinediones of this invention.

The novel intermediate compounds are represented by the formula II:

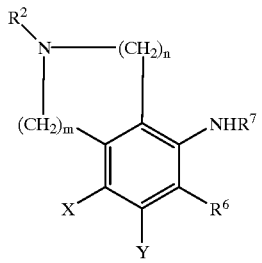

(II)

wherein X and Y are as previously described;

R⁶ is NO₂ or NH₂; R⁷ is hydrogen or an acetyl group; R⁸ is hydrogen, alkylCOOR³, alkylamine, alkylquanidine, W, W-alkyl, COalkyl, COalkyl-W, CONR³-W, CONR³aryl, CONR³alkyl-W, CSNR³aklyl, CSNR³alkyl-W or a common amino acid moiety joined by an amide bond, wherein R³ is as previously described, and m and n are independently 0, 1 or 2 provided that m+n is >1 and provided that when X is hydrogen then R⁶ is NH₂. Preferred intermediates of this invention includes those illustrated by formula II wherein Y is hydrogen, X is Br or hydrogen and (i) m is 1 and n is 2 or (ii) m is 2 and n is 1.

DETAILED DESCRIPTION OF THE PREFERRED EMBODIMENTS

The N-substituted azacycloalkyl ring fused quinoxalinediones of this invention are represented by previously defined formula I.

Preferably, X and Y are independently hydrogen, bromo and nitro and most preferably X is nitro and Y is hydrogen. It is also preferred that the azacycloalkyl ring is a six membered ring and most preferably (i) m is 1 and n is 2 or (ii) m is 2 and n is 1.

In the present invention $R^2$ is not hydrogen, alkyl or alkoxy. Preferable examples of $R^2$ include, for example,

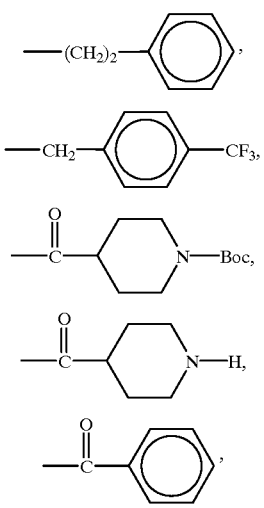

-continued

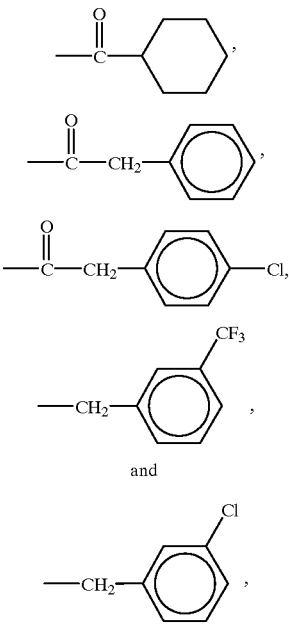

wherein z is 1–3.

Exemplary preferred compounds of Formula I include, without limitation:

6-Bromo-1,4,7,8,9,10-hexahydro-9-(phenylmethyl)pyrido[3,4-f]quinoxaline-2,3-dione
6-Bromo-1,4,7,8,9,10-hexahydro-9-(2-phenylethyl)pyrido[3,4-f]quinoxaline-2,3-dione;
6-Bromo-1,4,7,8,9,10-hexahydro-9-(3-phenylpropyl)pyrido[3,4-f]quinoxaline-2,3-dione;
1,4,7,8,9,10-Hexahydro-9-[[4-(trifluoromethyl)phenyl]methyl]pyrido[3,4-f]quinoxaline-2,3-dione;
1,4,7,8,9,10-Hexahydro-6-nitro-9-[[4-trifluoromethyl)phenyl]methyl]pyrido[3,4-f]quinoxaline-2,3-dione;
1,4,7,8,9,10-Hexahydro-9-[[4-(trifluoromethyl)phenyl]methyl]pyrido[3,4-f]quinoxaline-2,3-dione methanesulfonate (1:1) salt;
1,4,7,8,9,10-Hexahydro-8-[[4-(trifluoromethyl)phenyl]methyl]pyrido[4,3-f]quinoxaline-2,3-dione;
1,4,7,8,9,10 Hexahydro-6-nitro-8-[[4-(trifluoromethyl)phenyl]methyl]pyrido[4,3-f]quinoxaline-2,3-dione;
1,4,7,8,9,10-Hexahydro-6-nitro-8-[[4-(trifluoromethyl)phenyl]methyl]pyrido[4,3-f]quinoxaline-2,3-dione methanesulfonate (1:1)salt;
1,1-dimethylethyl 4-[(1,2,3,4,7,8,9,10-octahydro-2,3-dioxopyrido[3,4-f]quinoxaline-9-yl)carbonyl]-1-piperidine carboxylate;
1,4,7,8,9,10-Hexahydro-9-(4-piperidinylcarbonyl)pyrido[3,4-f]quinoxaline-2,3-dione;
1,1-dimethylethyl 4-[(1,2,3,4,7,8,9,10-octahydro-6-nitro-2,3-dioxopyrido[3,4-f]quinoxaline-9-yl)carbonyl]-1-piperidine carboxylate;
9-Benzoyl-1,4,7,8,9,10-hexahydro-6-nitropyrido[3,4-f]quinoxaline-2,3-dione;
9-(Cyclohexylcarbonyl)-1,4,7,8,9,10-hexahydro-6-nitropyrido[3,4-f]quinoxaline-2,3-dione;
9-(4-Chlorobenzoyl)-1,4,7,8,9,10-hexahydro-6-nitropyrido[3,4-f]quinoxaline-2,3-dione;
1,4,7,8,9,10-Hexahydro-6-nitro-9-(phenylacetyl)pyrido[3,4-f]quinoxaline-2,3-dione;
9-[(4-chlorophenyl)acetyl]-1,4,7,8,9,10-hexahydro-6-nitropyrido[3,4-f]quinoxaline-2,3-dione;

6-Bromo-1,4,7,8,9,10-hexahydro-8-(phenylmethyl)pyrido[3,4-f]quinoxaline-2,3-dione hydrochloride;

6-Bromo-1,4,7,8,9,10-hexahydro-8-(2-phenylethyl)pyrido[3,4-f]quinoxaline-2,3-dione hydrochloride;

6-Bromo-1,4,7,8,9,10-Hexahydro-8-[[3-(trifluoromethyl)methyl]pyrido[3,4-f]quinoxaline-2,3-dione hydrochloride;

6-Bromo-1,4,7,8,9,10-hexahydro-8-[(3-chlorophenyl)methyl]pyrido[3,4-f]quinoxaline-2,3-dione hydrochloride; and 6-Bromo-1,4,7,8,9,10-hexahydro-8-(3-phenylpropyl)pyrido[3,4-f]quinoxaline-2,3-dione hydrochloride.

This invention is also directed to methods for preparing the N-substituted azacyclo fused ring 2,3-quinoxalinedione compounds of formula I. Exemplary reaction Schemes T and III in conjunction with Schemes II and IV, respectively, illustrate the preparation of the compounds of this invention having a substituted nitrogen at the 8 and 9 position of the azacycloalkyl fused ring 2,3-quinoxalinedione compounds. The starting materials employed in Schemes I and III are readily available or can be prepared by known methods while the starting materials of schemes II and IV can be derived, respectively, by the methods set forth in Schemes I and III.

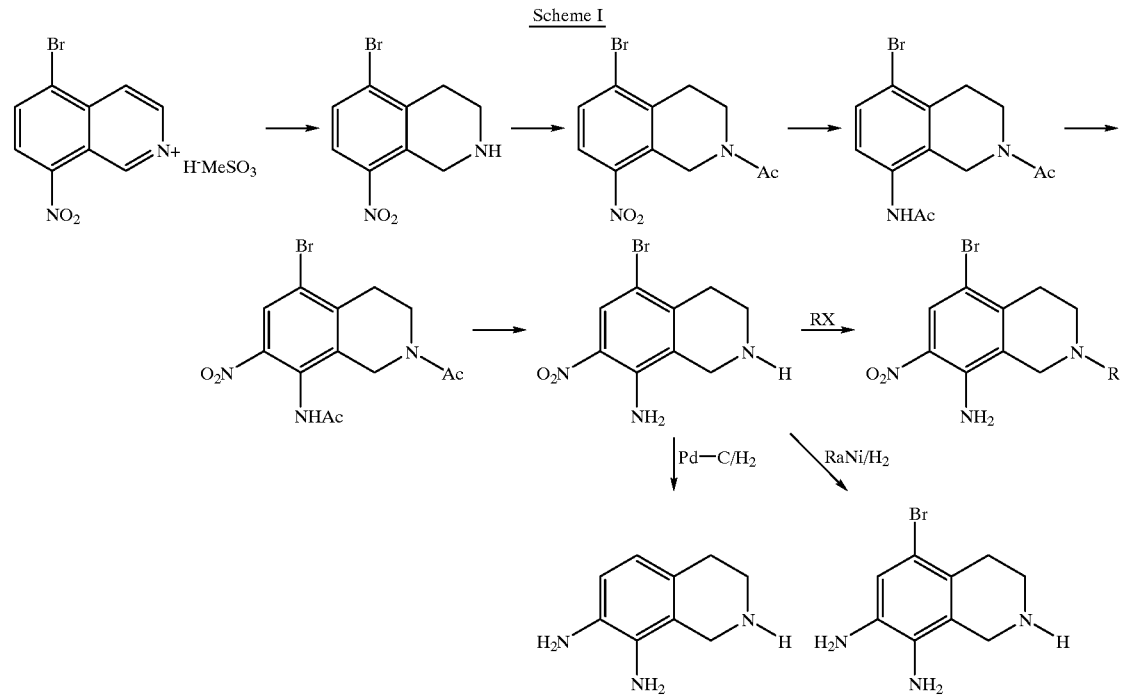

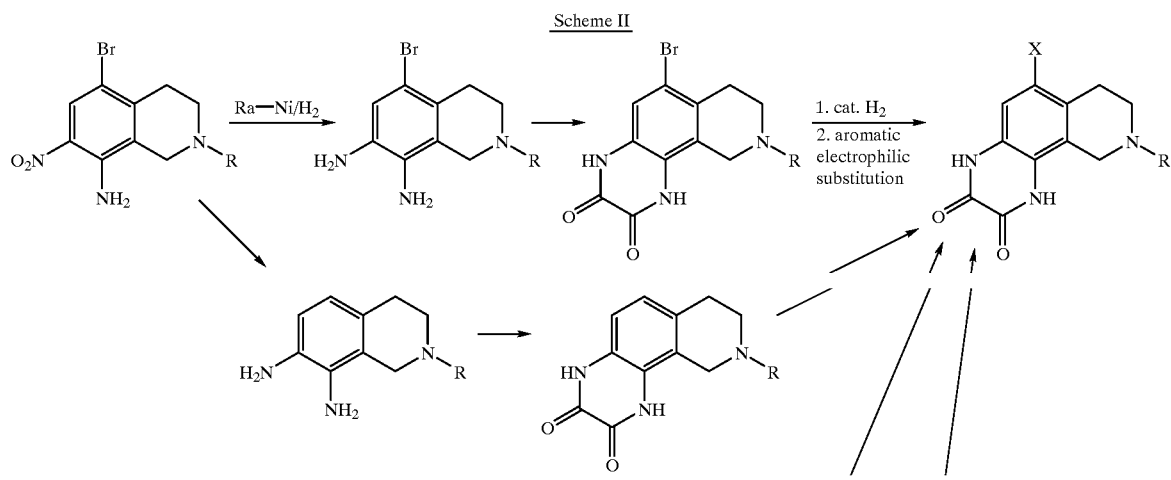

13
14
-continued
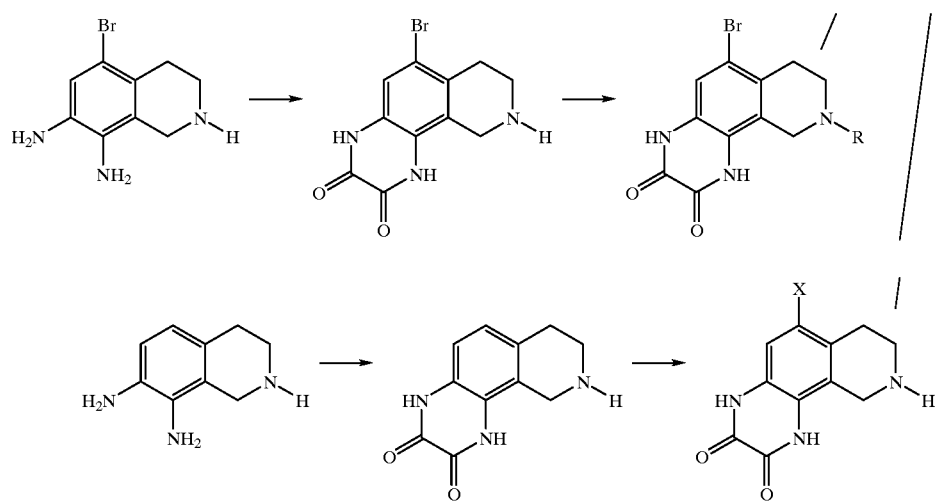
Scheme III
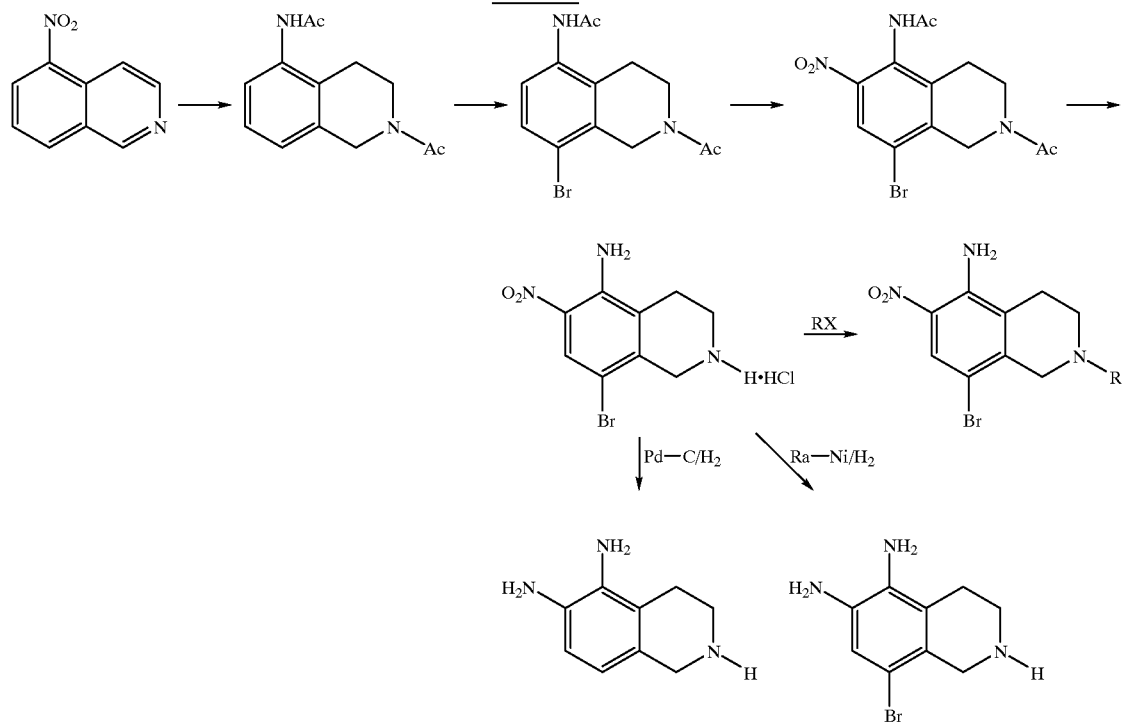

Scheme IV

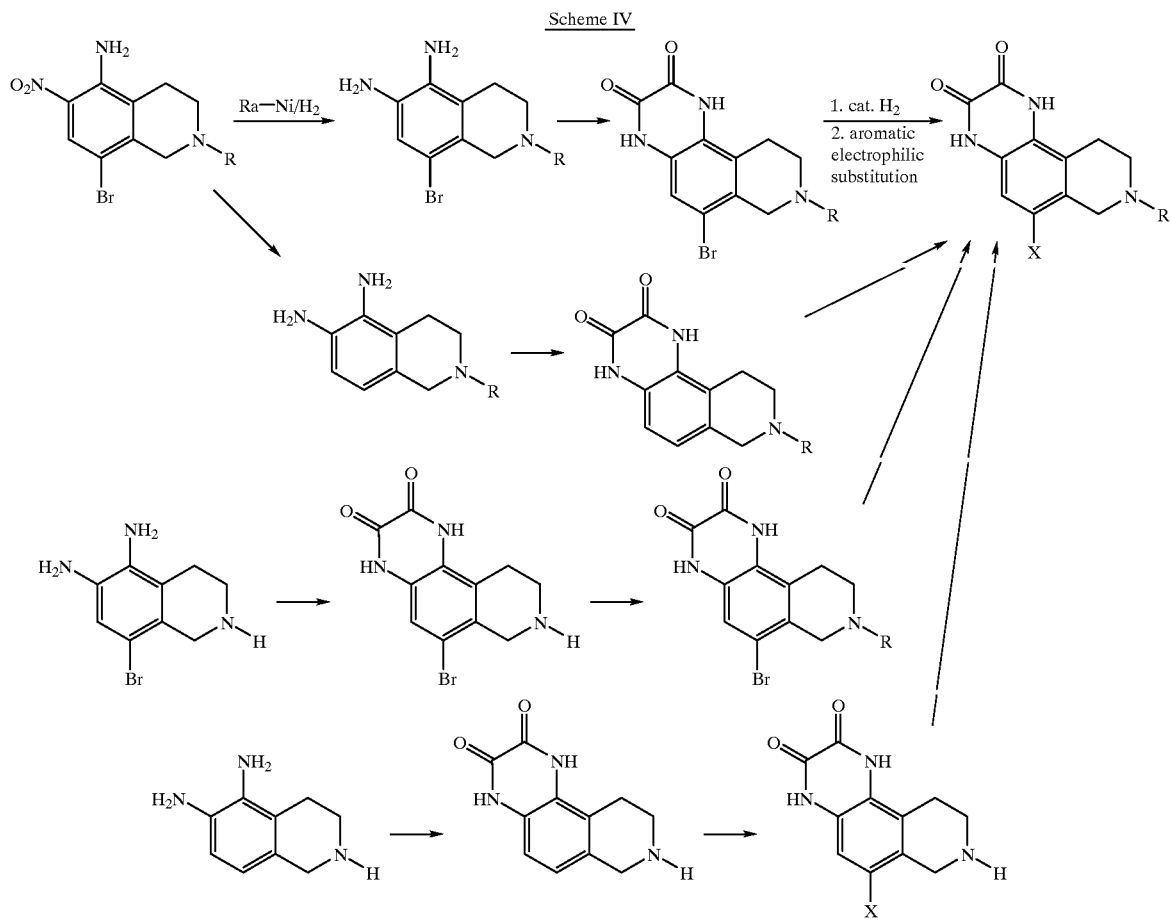

A preferred method for preparing the compound of formula (I) comprises the steps of:
(a)(i) hydrogenating and acetylating an aromatic nitro group of a compound of formula

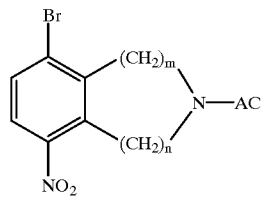

wherein m and n is 0, 1 or 2, or
(ii) halogenating a compound of formula

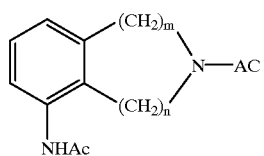

wherein m and n are as previously described, to form a compound of formula

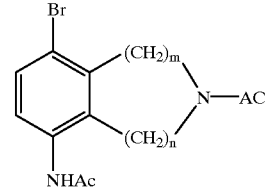

(b) nitrating the compound formed in step (a) to produce a compound of formula

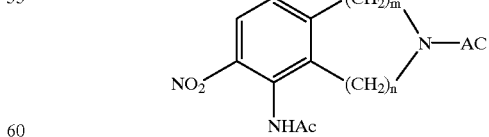

(c) deacetylating the compound of step (b) to produce a compound of formula

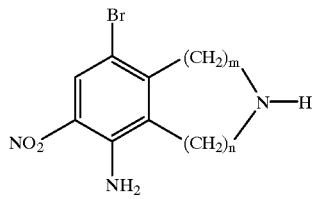

(d) treating the compound of step (c) by either (i) reaction with $R^2X^3$ wherein $R^2$ is the same as defined for formula (I) and $X^3$ is a leaving group, or alternatively reaction with $R^{2'}CHO$ or $R^{2'}COR^{2''}$ in the presence of a reducing agent such as, for example, sodium cyanoborohydride in a solvent such as methanol or tetrahydrofuran wherein $R^{2'}$ and $R^{2''}$ are the same as $R^2$, to produce a compound of formula

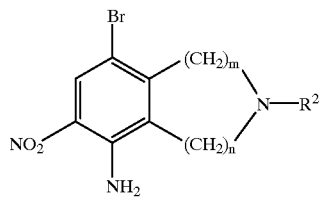

(ii) a non-dehalogenating hydrogenation to produce a compound of formula

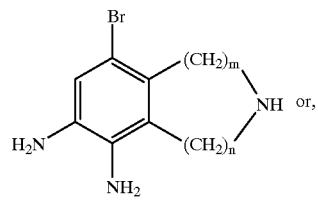

(iii) a dehalogenating hydrogenation to produce a compound of formula

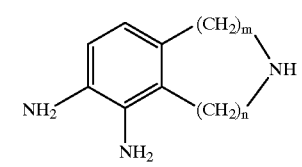

(e) if the compound of step (f)(i) is produced, treating that compound by either (i) a non-dehalogenating hydrogenation to produce a compound of formula

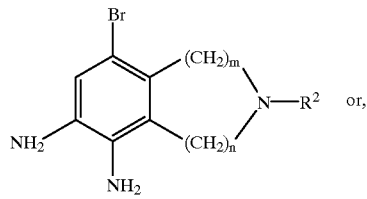

(ii) a dehalogenating hydrogenation to produce a compound of formula

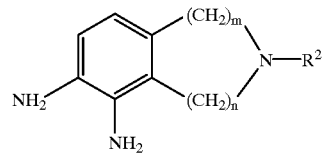

(f) condensation of the compound of any of steps (d)(ii), (d)(iii), (e)(i) or (e)(ii) with oxalic acid or an oxalic acid ester to produce a compound of formula

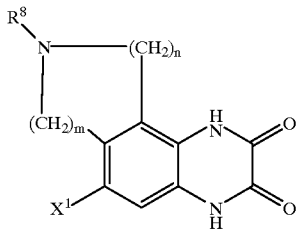

wherein $R^8$ is the same as defined for formula (II) and $X^1$ is hydrogen or bromo, (g) optionally reacting the compound of step (f) with an aromatic electrophillic substituent to produce a compound of formula

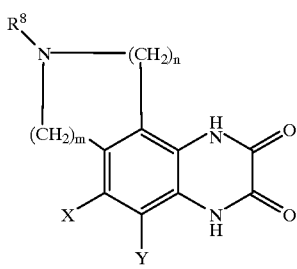

wherein X and Y are the same as defined for formula (I)

(h) optionally reacting the compound of steps (f) or (g) wherein $R^8$ is hydrogen with $R^2X^3$ wherein $R^2$ and $X^3$ are as previously described, or alternatively with $R^{2'}CHO$ or $R^{2'}COR^{2''}$ in the presence of a reducing agent such as, for example, sodium cyanoborohydride in a solvent such as methanol or tetrahydrofuran wherein $R^{2'}$ and $R^{2''}$ are as previously described, to produce a compound of formula

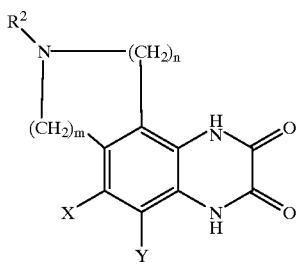

wherein $R^2$, X and Y are as previously described with the exception that if the compound of step (f) wherein $R^8$ is hydrogen is reacted then X is $X^1$ and Y is hydrogen, (i) optionally reacting the compound of step (h) wherein X is X¹ and Y is hydrogen with an aromatic electrophillic substituent to produce a compound of formula

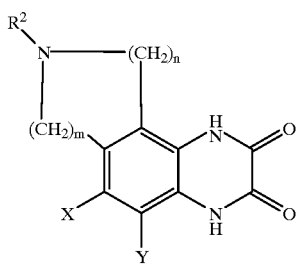

wherein X and Y are as described for the compound of formula (I).

Examples of preferred $R^2X^3$ and $R^{2o}$ CHO reactants include, without limitation, benzaldehyde, phenylacetylaldehyde, hydrocinnamaldehyde, α,α,α-trifluro-p-tolualdehyde, N-Boc-4-piperidinecarboxylic acid, a CDI (carbonyldiimidazole) adduct of benzoic acid, a CDI adduct of chlorobenzoic acid, a CDI adduct of phenylacetic acid, a CDI adduct of (4-chlorophenyl)acetic acid, 3-trifluoromethyl-benzaldehyde, 3-chlorobenzaldehyde and phenylpropioaldehyde.

The methods set forth herein, may also be employed to prepare novel intermediates of this invention. The preferred novel intermediates include:

N-(2-Acetyl-5-bromo-1,2,3,4-tetrahydro-8-isoquinolinyl)-acetamide;
N-(2-Acetyl-5-bromo-7-nitro-1,2,3,4-tetrahydro-8-isoquinolinyl)-acetamide;
5-Bromo-7-nitro-1,2,3,4-tetrahydro-8-isoquinolinylamine monohydrochloride;
5-Bromo-1,2,3,4-tetrahydro-7-nitro-2-(phenylmethyl)-8-isoquinolinamine;
5-Bromo-1,2,3,4-tetrahydro-2-(phenylmethyl)-7,8-isoquinolinediamine;
5-Bromo-1,2,3,4-tetrahydro-7-nitro-2-(2-phenylethyl)-8-isoquinolinamine;
5-Bromo-1,2,3,4-tetrahydro-2-(2-phenylethyl)-7,8-isoquinolinediamine;
5-Bromo-1,2,3,4-tetrahydro-7-nitro-2-(3-phenylpropyl)-8-isoquinolinamine;
5-Bromo-1,2,3,4-tetrahydro-2-(3-phenylpropyl)-7,8-isoquinolinediamine;
5-Bromo-1,2,3,4-tetrahydro-7-nitro-2-[[4-(trifluoromethyl)phenyl]methyl]-8-isoquinolinamine;
1,2,3,4-Tetrahydro-2-[[4-(trifluoromethyl)phenyl]methyl]-7,8-isoquinolinediamine;
N-(2-Acetyl-8-bromo-1,2,3,4-tetrahydro-5-isoquinolinyl)acetamide;
N-(2-Acetyl-8-bromo-6-nitro-1,2,3,4-tetrahydro-5-isoquinolinyl)acetamide;
8-Bromo-6-nitro-1,2,3,4-tetrahydro-5-isoquinolinamine hydrochloride;
8-Bromo-1,2,3,4-tetrahydro-6-nitro-2-[[4-(trifluoromethyl)phenyl]methyl]-5-isoquinolinamine;
1,2,3,4-Tetrahydro-2-[[4-(trifluoromethyl)phenyl]methyl]-5,6-isoquinolinediamine monohydrobromide;
1,2,3,4-Tetrahydro-7,8-isoquinolinediamine monohydrobromide monohydrochloride;
8-Bromo-1,2,3,4-tetrahydro-6-nitro-2-(phenylmethyl)-5-isoquinolinamine;
8-Bromo-1,2,3,4-tetrahydro-2-(phenylmethyl)-5,6-isoquinolinediamine;
8-Bromo-1,2,3,4-tetrahydro-6-nitro-2-(2-phenylethyl)-5-isoquinolinamine;
8-Bromo-1,2,3,4-tetrahydro-2-(2-phenylethyl)-5,6-isoquinolinediamine;
8-Bromo-1,2,3,4-tetrahydro-6-nitro-2-[[3-(trifluoromethyl)phenyl]methyl]-5-isoquinolinamine;
8-Bromo-1,2,3,4-tetrahydro-2-[[3-(trifluoromethyl)phenyl]methyl]-5,6-isoquinolinediamine;
8-Bromo-1,2,3,4-tetrahydro-6-nitro-2-[(3-chlorophenyl)methyl]-5-isoquinolinamine;
8-Bromo-1,2,3,4-tetrahydro-2-[(3-chlorophenyl)methyl]-5,6-isoquinolinediamine;
8-Bromo-1,2,3,4-tetrahydro-6-nitro-2-[3-phenylpropyl]-5-isoquinolinamine; and
8-Bromo-1,2,3,4-tetrahydro-2-[3-phenylpropyl]-5,6-isoquinolinediamine.

The compounds of the invention exhibit valuable biological properties because of their strong excitatory amino acid (EAA) antagonizing properties at one of several binding sites on glutamate receptors: the AMPA ((RS)—amino-3-hydroxy-5-methyl-4-isoxazolepropionic acid (or kainic acid) binding site on AMPA (non-NMDA) receptors or the glycine site of NMDA receptors. The compounds generally have activity at both NMDA and non-NMDA receptors, and thus may act in disorders arising from over excitation of either receptor family.

The compounds of the present invention exhibit binding affinity for the AMPA receptors as described by Honoré T., et al., *Neuroscience Letters* 1985; 54:27–32. Preferred compounds demonstrate $IC_{50}$ values <100 μM in this assay. The compounds of the present invention exhibit binding affinity for the kainate site (non-NMDA receptor) as described by London, ED and Coyle, J, *Mol. Pharmacol,* 1979; 15:492. The compounds of the present invention exhibit binding affinity for the glycine site of the NMDA receptor as described by Jones, S M et al., *Pharmacol. Methods* 1989; 21:161. To measure functional AMPA antagonist activity, the effects of the agent on AMPA-induced neuronal damage in primary cortical neuronal cultures was examined using techniques similar to those outlined by Koh, J. -Y. et al., *J. Neurosci,* 1990; 10:693. In addition, the neuronal damage produced by long-term exposure to 100 μM AMPA may be measured by the release of the cytosolic enzyme lactate dehydrogenase (LDH).

Selected compounds of the present invention were tested by one or more of the above-described assays. The data obtained in these assays is set forth in Table 1. The $IC_{50}$ values set forth in Table 1 are a measure of the concentration (μM) of the test substance which inhibits 50% of an induced release from the tested receptors.

TABLE 1

N-Substituted Azacycloalkyl
Ring Fused Quinoxalinediones

| Compound of Example | AMPA ($IC_{50}$ μM) | Kainate ($IC_{50}$ μM) | Glycine (% Inhibition at 10 μM) |
|---|---|---|---|
| (8) | 20 | 16 | <50 |
| (11) | >100 | 9 | <50 |
| (14) | 100 | 40 | <50 |
| (17) | 100 | >100 | |
| (18) | 3.1 | 34 | |
| (26) | >100 | >100 | |
| (30) | 84 | 56 | |
| (31) | 51 | .48 | 70 |
| (32) | >100 | 65 | |

TABLE 1-continued

N-Substituted Azacycloalkyl Ring Fused Quinoxalinediones

| Compound of Example | AMPA (IC$_{50}$ μM) | Kainate (IC$_{50}$ μM) | Glycine (% Inhibition at 10 μM) |
|---|---|---|---|
| (34) | 0.58 | 6.9 | 81 |
| (35) | 0.37 | 1.38 | 80 |
| (36) | 0.34 | 5.87 | 88 |
| (37) | 0.84 | 8.2 | 74 |
| (38) | 0.24 | 1.62 | 99 |
| (39) | 0.84 | 8.2 | 98 |
| (48) | 21 | 67 | |
| (54) | 43 | >100 | |

Additionally, as a preliminary indicator of in vivo CNS activity related to anticonvulsant activity and potential neuroprotection, a maximal electroshock assay in CF-1 strain mice (20–25 g) was performed with corneal electrodes by conventional methods as described previously (Krall et al., *Epilepsia* 1988; 19:409–428. The compounds of this invention generally demonstrated ED$_{50}$ values of <50 mg/kg.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The examples which follow are intended as an illustration of certain preferred embodiments of the invention, and no limitation of the invention is implied.

EXAMPLE 1

5-Bromo-1,2,3,4-tetrahydro-8-nitroisoquinoline

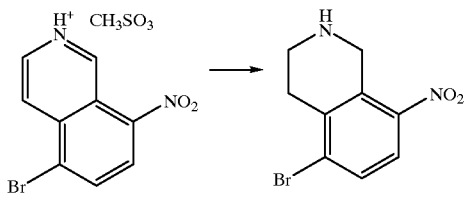

5-Bromo-8-nitro-2-isoquinolium methanesulfonate (1 g, 2.9 mmol) was dissolved in acetic acid (10 mL) and sodium cyanoborohydride (0.4 g, 6.4 mmol) was added at 0° C. The mixture was stirred at 0° C. for 50 min. The reaction was quenched with ice-cold water (~5 mL), stirred in an ice/water bath and basifyied to pH 10 with ammonium hydroxide. After being stirred for 4 hours the solids were filtered, dissolved in chloroform, dried over MgSO$_4$ and activated charcoal, filtered, and evaporated under vacuum to give the substituted tetrahydroisoquinoline (0.5 g, 68% yield) as a tan solid, mp =78–81° C.

Analysis for (C$_9$H$_9$N$_2$O$_2$Br): Calc.: C, 42.05; H. 3.53; N. 10.90. Found: C, 42.07; H. 3.52; N. 10.71.

EXAMPLE 2

1-(5-Bromo-8-nitro-3,4-dihydro-1H-isoquinolin-2-yl)-ethanone

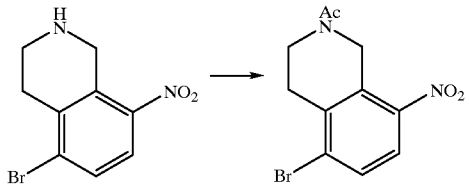

The product from Example 1 (17.6 g, 68.5 mmol) was dissolved in THF (50 mL), treated with acetic anhydride (100 mL), stirred at room temperature under nitrogen for 21 hours and evaporated under vacuum. The residue was chromatographed on silica gel (33W ethyl acetate in hexane graduated to pure ethyl acetate) to give the title compound (11.35 g, 55% yield) as a brown solid, mp=159–161° C.

EXAMPLE 3

N-(2-Acetyl-5-bromo-1,2,3,4-tetrahydro-8-isoqinolinyl)-acetamide

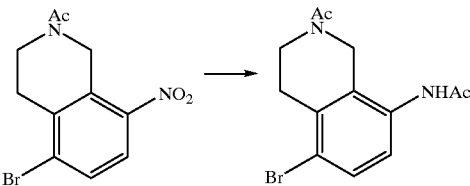

The product from Example 2 (13.05 g, 43.6 mmol) was dissolved in THF (100 mL) and treated with Raney Nickel (2 g). Under the presence of hydrogen (19.8 psi, 23° C.) the mixture was stirred for 19 hours, and evaporated under vacuum. The residue was then washed with diethyl ether and evaporated under vacuum to give a semi-solid. The semi-solid was treated with acetic anhydride (30 mL), THF (30 mL) and stirred. After 2 hours the solvent was evaporated under vacuum. The residue was dissolved in THF, dried with $MgSO_4$, activated charcoal, and passed through a plug of silica gel eluted with ethyl acetate. Upon evaporation under vacuum the desired product was isolated (14.6 g, 96% yield) as a tan solid, mp=127–130° C.

EXAMPLE 4

N-(2-Acetyl-5-bromo-7-nitro-1,2,3,4-tetrahydro-8-isoquinolinyl)-acetamide

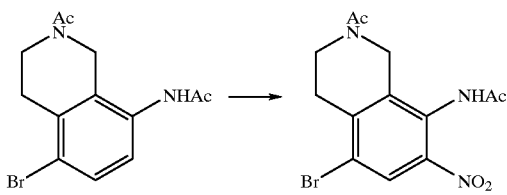

A solution of the product from Example 4 (2.1 g, 6.75 mmol) in trifluoroacetic acid (20 mL) was treated with fuming nitric acid (5 mL). The resulting solution was stirred at room temperature for 15 hours then evaporated under vacuum. The residue was dissolved in water (10 mL) and basifyied to pH 9 with ammonium hydroxide. After stirring for two hours in an ice/water bath the solids were filtered off, dissolved in dichloromethane, dried over $MgSO_4$, filtered and evaporated under vacuum. After triturating in dichloromethane, the solids were filtered, washed with hexane and dried to give the desired product (2 g, 80% yield) as a yellow solid, mp=173–175° C.

EXAMPLE 5

5-Bromo-7-nitro-1,2,3,4-tetrahydro-8-isoquinolinylamine monohydrochloride

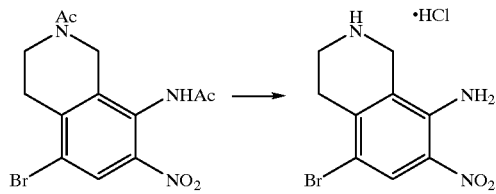

A solution of the product from Example 4 (11.7 g, 32.8 mmol) and 3N HCl (400 mL) was heated to reflux for 4 hours. Upon cooling to room temperature, the solids were filtered, washed with 3N HCl and diethyl ether, and air dried to give the title compound (7.8 g, 77% yield) as a yellow solid, mp-305–307° C.

EXAMPLE 6

5-bromo-1,2,3,4-tetrahydro-7 nitro-2 (phenylmethyl)-8-isoquinolinamine

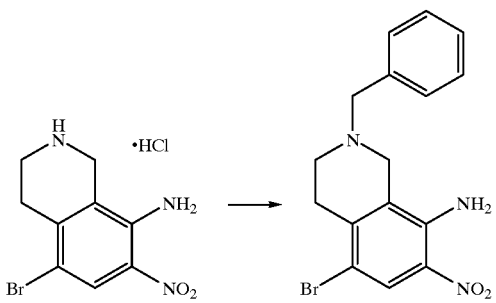

A solution of the product from Example 5 (1 g, 3.24 mmol) and benzaldehyde (0.71 mL, 7 mmol) in 2:1 MeOH/$H_2O$ (50 mL) was treated with sodium cyanoborohydride (0.56 g, 9 mmol) portionwise under nitrogen and stirred for six hours. The reaction mixture was then added to dichloromethane (150 mL) and washed with saturated sodium bicarbonate. The organic layer was dried over magnesium sulfate and activated charcoal, filtered through a plug of silica gel and concentrated under vacuum to dryness. The solids were triturated in hexane, filtered, and oven dried to give the title compound (0.73 g, 62% yield) as an orange solid, mp=150–152° C.

Analysis for ($C_{16}H_{16}BrN_3O_2$): Cal.: C, 53.05; H, 4.45; N, 11.60. Found: C, 52.44; H, 4.38; N, 11.44.

EXAMPLE 7

5-Bromo-1,2,3,4-tetrahydro-2-(phenylmethyl)-7,8-isoquinolinediamine

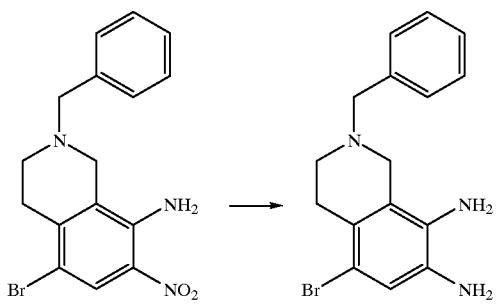

A solution of the product from Example 6 (0.7 g, 1.93 mmol) in THF (60 mL) was stirred over RaNi under a hydrogen balloon for 40 mins. The catalyst was filtered off and concentrated under vacuum to give the title compound (0.64 g, 99% yield) as a light purple oil.

EXAMPLE 8

6-Bromo-1,4,7,8,9,10-hexahydro-9-(phenylmethyl)pyrido[3,4-f]quinoxaline-2,3-dione

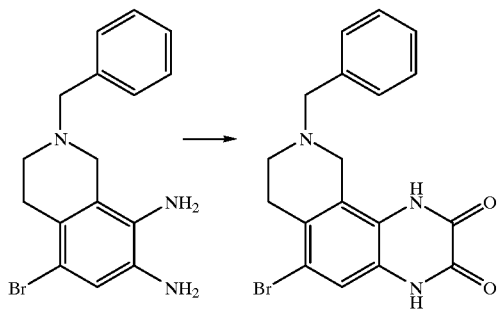

A solution of the product from Example 7 (0.64 g, 1.93 mmol) in 3N HCl (25 mL) was treated with oxalic acid (0.37 g, 2.9 mmol) and refluxed for four hours. When cool to room temperature the precipitate was filtered, suspended in water (70 mL) and basifyed to pH 10. The solids were filtered, and dried to give the title compound (0.57 g, 89%) as a light brown solid, mp=297–302° C.

EXAMPLE 9

5-Bromo-1,2,3,4-tetrahydro-7-nitro-2-(2-phenylethyl)-8-isoquinolinamine

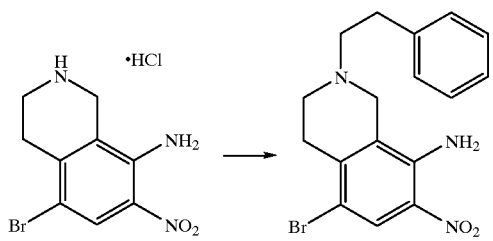

A solution of the product from Example 5 (1 g, 3.24 mmol) and phenylacetylaldehyde (0.82 ml, 7 mmol) in 2:1 MeOH/H$_2$O (50 mL) was treated with sodium cyanoborohydride (0.56 g, 9 mmol) portionwise under nitrogen and stirred for one hour. The reaction mixture was then cooled under an ice bath and precipitate filtered off. The solids were washed with hexane and oven dried to give the title compound (1.16 g, 95% yield) as an orange solid, mp=120–122° C.

Analysis for (C$_{16}$H$_{16}$BrN$_3$O$_2$) Calc.: C, 54.27; H, 4.82; N, 11.17. Found: C, 53.93; H, 4.63; N, 10.88.

EXAMPLE 10

5-Bromo-1,2,3,4-tetrahydro-2-(2-phenylethyl)-7,8-isoquinolinediamine

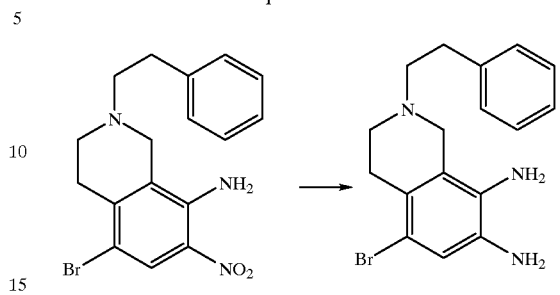

A solution of the product from Example 9 (0.6 g, 1. mmol) in THF (50 mL) was stirred over RaNi under a hydrogen balloon for 40 mins. The catalyst was filtered off and concentrated under vacuum to give the title compound (0.54 y, 98% yield) as a pink solid.

EXAMPLE 11

6-Bromo-1,4,7,8,9,10-hexahydro-9-(2-phenylethyl)pyrido[3,4-f]quinoxaline-2,3-dione

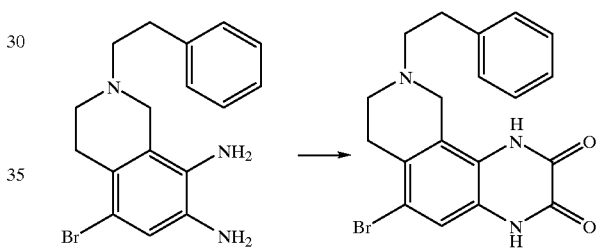

A solution of the product from Example 10 (0.54 g, 1.56 mmol) in 3N HCl (20 mL) was treated with oxalic acid (0.3 b, 2.34 mmol) and refluxed for four hours. When cool to room temperature the precipitate was filtered, suspended in water (70 mL) and basifyed to pH 10. The solids were filtered, and dried to give the title compound (0.37 g, 60%) as a brown solid, mp=290–295° C.

EXAMPLE 12

5-Bromo-1,2,3,4-tetrahydro-7-nitro-2-(3-phenylpropyl)-8-isoquinolinamine

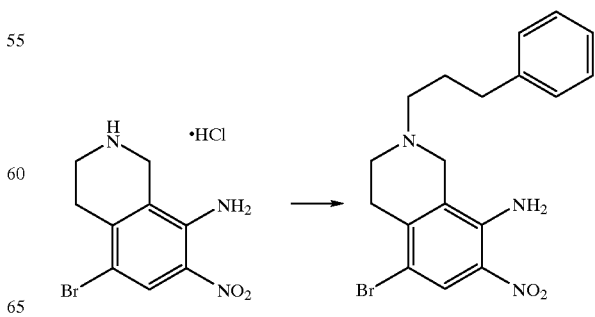

A solution of the product from Example 5 (1 g, 3.24 mmol) and hydrocinnamaldehyde (0.94 g, 7 mmol) in 2:1 MeOH/H$_2$O (50 mL) was treated with sodium cyanoborohydride (0.56 g, 9 mmol) portionwise under nitrogen and stirred for six hours. The solvent was decanted and the semi-solid was dissolved in dichloromethane, dried over magnesium sulfate, filtered and concentrated under vacuum. The crude compound was chromatographed on silica gel (eluted with 25% ethyl acetate in hexane) to give the title compound (1.18 g, 94% yield) as a brown oil.

EXAMPLE 13

5-Bromo-1,2,3,4-tetrahydro-2-(3-phenylpropyl)-7,8-isoquinolinediamine

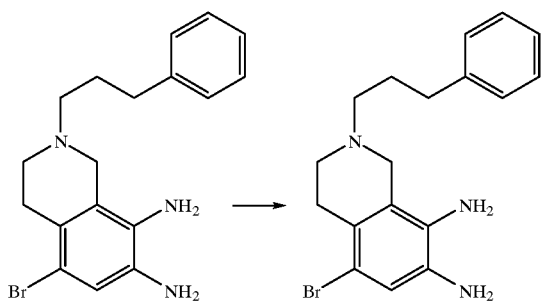

A solution of the product from Example 12 (1.1 g, 2.82 mmol) in THF (80 mL) was stirred over RaNi under a hydrogen balloon for 19 hours. The catalyst was filtered off and concentrated under vacuum to give the title compound (0.98 g, 96% yield) as a dark brown oil.

EXAMPLE 14

6-Bromo-1,4,7,8,9,10-hexahydro-9-(3-phenylpropyl) pyrido[3,4-f]quinoxaline-2,3-dione

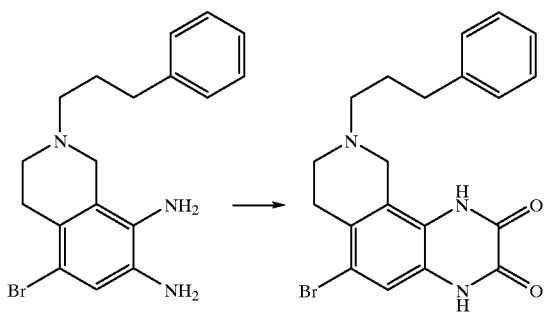

A solution of the product from Example 12 (0.98 g, 2.72 mmol) in 3N HCl (35 mL) was treated with oxalic acid (0.36 g, 2.86 mmol) and refluxed for five hours. When cool to room temperatures the precipitate was filtered, suspended in water (70 mL) and basifyed to pH 8. The solids were filtered, and dried to give the title compound (0.68 g, 60%) as a brown solid, mp=288–293° C.

EXAMPLE 15

5-Bromo-1,2,3,4-tetrahydro-7-nitro-2-[[(4-(trifluoromethyl)phenyl]methyl]-8-isoquinolinamine

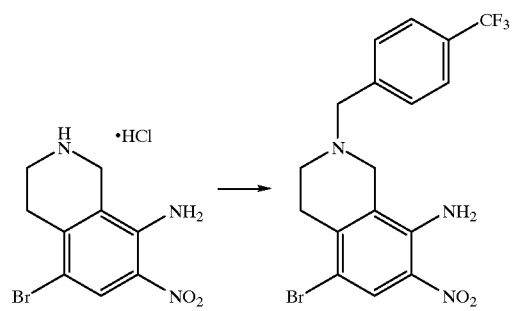

A solution of the product from Example 5 (1 g, 3.24 mmol) and α,α,α-trifluro-p-tolualdehyde (1.22 g, 7 mmol) in 2:1 MeOH/H$_2$O (50 mL) was treated with sodium cyanoborohydride (0.56 g, 9 mmol) portionwise under nitrogen and stirred for 2.5 hours. The precipitate was filtered, washed with hexane and dried to give the title compound (0.71 g, 51% yield) as a yellow solid, mp=119–120° C.

EXAMPLE 16

1,2,3,4-Tetrahydro-2-[[4-(trifluoromethyl)phenyl] methyl]-7,8-isoquinolinediamine

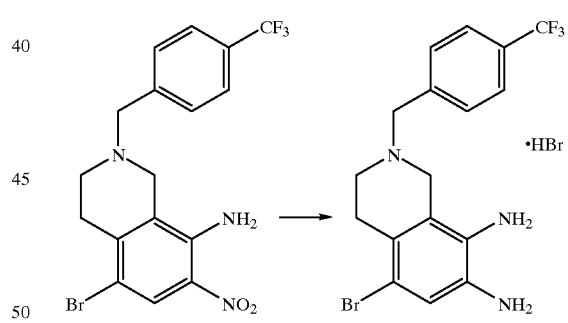

A solution of the product from Example 15 (0.6 g, 1.4 mmol) in methanol (100 mL) was shaken over 20% Pd/C under hydrogen and pressure for 2.3 hours. The catalyst was filtered off and concentrated under vacuum to give the title compound (0.53 g, 95% yield) as a dark red-brown solid, mp=130–135° C.

EXAMPLE 17

1,4,7,8,9,10-Hexahydro-9-[[4-(trifluoromethyl)phenyl]methyl]pryrido[3,4-f]quinoxaline-2,3-dione

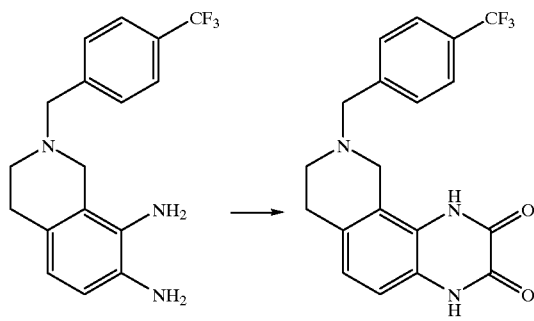

A solution of the product from Example 16 (0.53 g, 1.32 mmol) in 3N HCl (50 mL) was treated with oxalic acid (0.25 g, 1.98 mmol) and refluxed for four hours. After cooling to room temperature, the precipitate was filtered, suspended in water (70 mL), heated to 80° C. and basifyed to pH 8. The solids were filtered, and dried to give the title compound in two crops [125 mg, mp=293–297° C. (dec.)] and [33 mg, mp=263–266° C.(dec.)] yielding 34%.

EXAMPLE 18

1,4,7,8,9,10-Hexahydro-6-nitro-9-[[4-trifluoromethyl)phenyl]methyl]pyrido[3,4-f]quinoxaline-2,3-dione

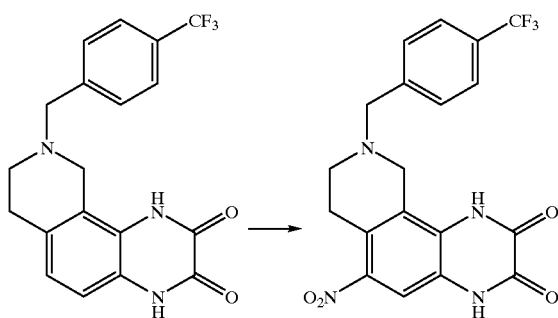

A solution of the product from Example 17 (90 mg, 0.24 mmol) in TFAA (5 mL) was treated with fuming nitric acid (115 µL, 2.56 mmol) and stirred under nitrogen for 19 hours. The resulting mixture was concentrated under vacuum and triturated with acetone. The solids were filtered and dried to give the title compound (90 mg, 90% yield) as an orange solid, mp=250–253° C.(dec.).

EXAMPLE 19

1,4,7,8,9,10-Hexahydro-9-[[4-trifluoromethyl)phenyl]methyl]pyrido[3,4-f]quinoxaline-2,3-dione methanesulfonate (1:1) salt

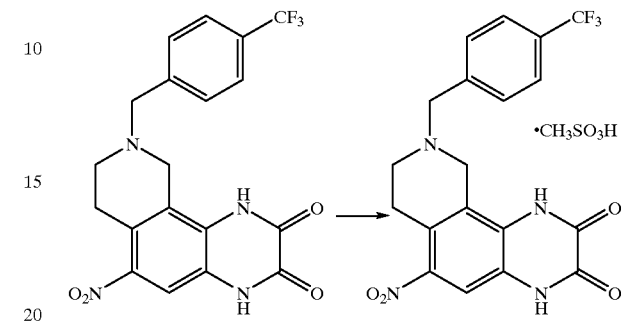

A solution of the product from Example 18 (76 mg, 0.18 mmol) in DMF (2 mL) was treated with methane sulfonic acid (12.3 µL, 0.19 mmol) and stirred at room temperature for 18 hours. The solids were filtered off, washed with ether and dried to give the first batch of the title compound (31 mg) as a yellow solid, mp=275–280° C. The filtrate was concentrated under vacuum, triturated with acetone. The precipitate was then filtered and dried to give the second batch of the title compound (17 mg) as a yellow solid, mp=199–204° C., 52% total yield.

EXAMPLE 20

N-(2-Acetyl-1,2,3,4-tetrahydro-5-isoquinolinyl)acetamiade

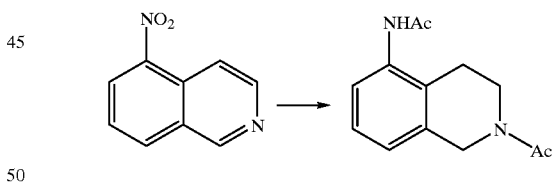

A mixture of 5-nitroisoquinoline (55.75 g) and 5% palladium on carbon (0.25 g) in acetic acid (1 L) and acetic anhydride (65 mL) was shaken on a Parr hydrogenation apparatus under a hydrogen atmosphere (50 psi) for 3.5 h. After removal of the catalyst, the filtrate was concentrated and the residue mixed with acetic anhydride (500 mL) and concentrated at 60° C. The residue was dissolved in chloroform (1 L), washed well with sodium bicarbonate solution, and then dried over magnesium sulfate. After evaporation, the residue was dissolved in ethyl acetate and concentrated to give an orange solid which was then recrystallized from tetrahydrofuran and washed with isopropyl ether to give a white solid (combined weight crop 1 & 2=44.86 g, 60% yield). mp 153–155° C.

EXAMPLE 21

N-(2-Acetyl-8-bromo-1,2,3,4-tetrahydro-5-isoquinolinyl)acetamide

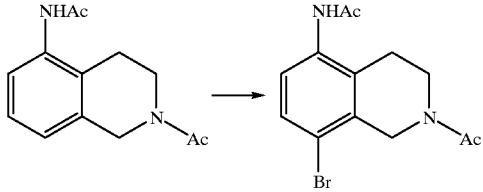

The product from Example 20 (20 g) was dissolved in 500 mL trifluoroacetic acid and treated dropwise with 100 mL of 1 M bromine in acetic acid. After stirring at room temperature, the reaction mixture was concentrated and dissolved in 500 mL chloroform and washed well with sodium bicarbonate solution. The aqueous layer was back-washed with chloroform, and the combined organic layers were dried over magnesium sulfate and evaporated. The residue was suspended in ethyl acetate and collected by filtration to give a white solid (21.47 g, 80% yield). mp =179–181° C.

EXAMPLE 22

N-(2-Acetyl-8-bromo-6-nitro-1,2,3,4-tetrahydro-5-isoquinolinyl)acetamide

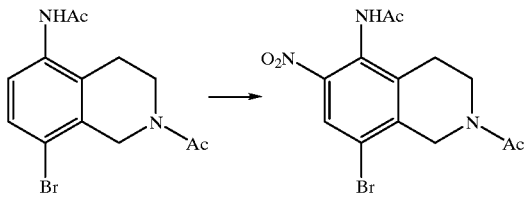

The product from Example 21 (31 g) was dissolved in trifluoroacetic acid (450 mL). The solution was treated dropwise with 33 mL of fuming 90% nitric acid and stirred at room temperature. The reaction mixture was concentrated, the residue was dissolved in chloroform and then washed well with sodium bicarbonate solution. A solid formed, and was dissolved in 3 L chloroform and dried over magnesium sulfate. After evaporation, the residue was crystallized from ethyl acetate to give a white solid (19.32 g), and the filtrate concentrated to give an additional 16.3 g.

EXAMPLE 23

8-Bromo-6-nitro-1,2,3,4-tetrahydro-5-isoquinolinamine hydrochloride

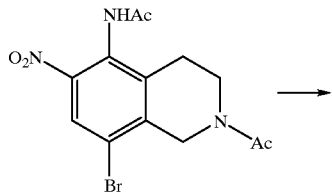

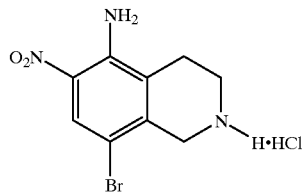

A mixture of the product from Example 22 (8.8 g, 24.7 mmol) in 100 mL 6 N HCl was heated at reflux for 2.5 h. After cooling in an ice bath, the yellow precipitate was collected by filtration, washed with diethyl ether and air dried to give 7.08 g of a yellow solid. The filtrate was concentrated to give a red orange solid (2.1 g).

EXAMPLE 24

8-Bromo-1,2,3,4-tetrahydro-6-nitro-2-[[4-(trifluoromethyl)phenyl]methyl]-5-isoquinolinamine

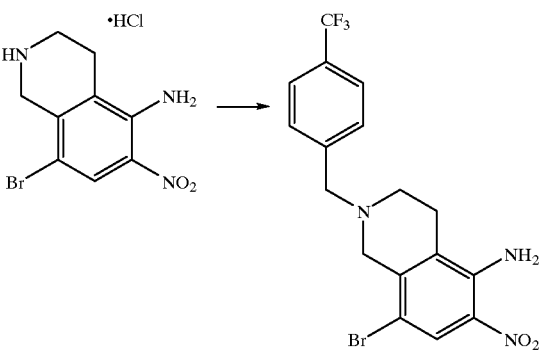

A solution of the product from Example 23 (1 g, 3.24 mmol) and α,α,α-trifuro-p-tolualdehyde (1.22 g, 7 mmol) in 2:1 MeOH/H$_2$O (50 mL) was treated with sodium cyanoborohydride (0.56 g, 9 mmol) portionwise under nitrogen and stirred for 2.5 hours. The reaction mixture was cooled under ice bath, after which the precipitant was filtered, and washed with hexane. The crude compound was purified via silica gel chromatography to give the title compound (0.95 g, 65% yield) as a yellow solid, mp=131–133° C.

EXAMPLE 25

1,2,3,4-Tetrahydro-2-[[4-(trifluoromethyl)phenyl]methyl]-5,6-isoquinolinediamine monohydrobromide

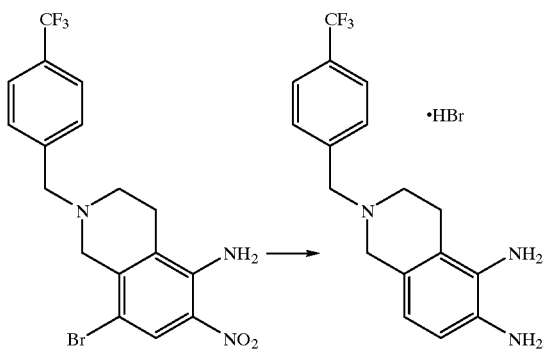

A solution of product from Example 24 (0.91 g, 2.1 mmol) in methanol (100 mL was shaken over 20% Pd/C under hydrogen and pressure for 15 minutes. The catalyst was filtered off and concentrated under vacuum to give the title compound (0.75 g, 88% yield) as a red-brown solid, mp=131–136° C.

EXAMPLE 26

1,4,7,8,9,10-Hexahydro-8-[[4-trifluoromethyl)phenyl]methyl]pyrido[4,3-f]quinoxaline-2,3-dione

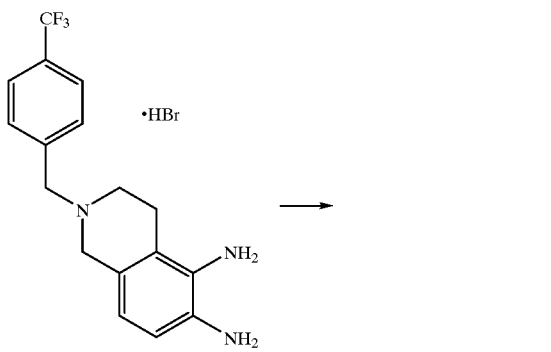

A solution of the product from Example 25 (0.75 g, 1.86 mmol) in 3N HCl (35 mL) was treated with oxalic acid (0.35 g, 2.8 mmol) and refluxed for four hours. When cool to room temperature the precipitate was filtered, suspended in water (70 mL), heated to 80° C. and basifyed to pH 10. The solids were filtered, and dried to give the title compound (256 mg, 37%).

EXAMPLE 27

1,4,7,8,9,10 Hexahydro-6-nitro-8-[[4-(trifluoromethyl)phenyl]methyl]pyrido[4,3-f]quinoxaline-2,3-dione

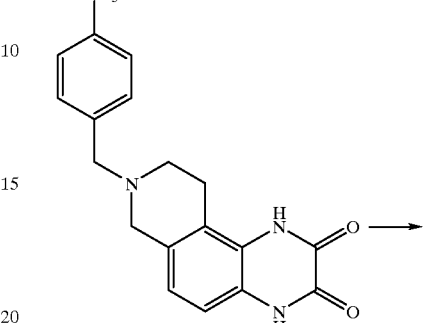

A solution of the product from Example 26 (180 mg, 0.48 mmol) in TFAA (10 mL) was treated with fuming nitric acid (225 µL, 5.04 mmol) and stirred under nitrogen for 5 days. The resulting mixture was concentrated under vacuum and triturated with acetone. The solids were filtered and dried to give the title compound (200 mg, 99% yield) as an orange solid, mp=230–233° C. (dec.).

EXAMPLE 28

1,4,7,8,9,10-Hexahydro-6-nitro-8-[[4-(trifluoromethyl)phenyl]methyl]pyrido[4,3-f]quinoxaline-2,3-dione methanesulfonate (1:1)salt

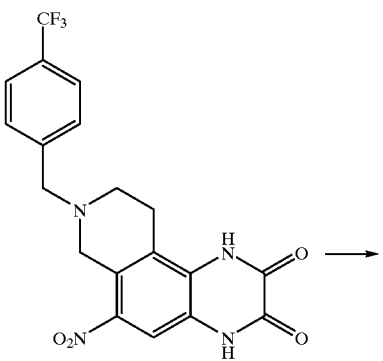

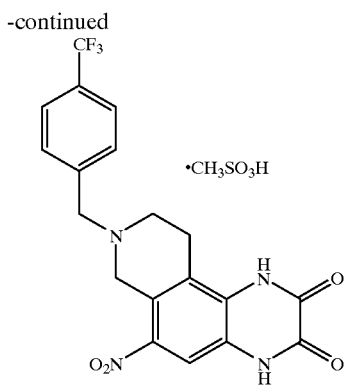

A solution of the product from Example 27 (185 mg, 0.44 mmol) in DMF (3 mL) was treated with methane sulfonic acid (30 μL, 0.46 mmol) and stirred at room temperature for 40 hours. The solids were filtered off, washed with DMF and dried to give the first batch of the title compound (39 mg) as a grey solid. The filtrate was concentrated under vacuum, triturated with acetone. The precipitate was then filtered and dried to give the second batch of the title compound (104 mg) as a pale yellow solid, mp=220–225° C., 46% total yield.

EXAMPLE 29

1,2,3,4-Tetrahydro-7,8-isoquinolinediamine monohydrobromide monohydrochloride

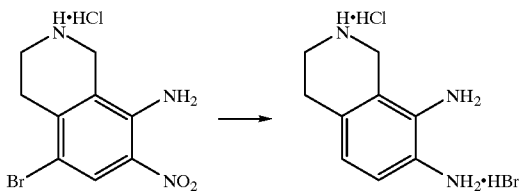

The product from Example 5 (7 g) in 250 mL of methanol was treated with 20% Pd/C (1 g) and shaken on a Parr apparatus under a hydrogen atmosphere (50 psi) for 16 h at ambient temperature. The catalyst was removed by filtration and the filtrate evaporated to give the product as a purple solid (6.3 g, 99% yield) that was used immediately without further purification.

EXAMPLE 30

1,4,7,8,9,10-Hexahydropyrido[3,4-f]quinoxaline-2,3-dione

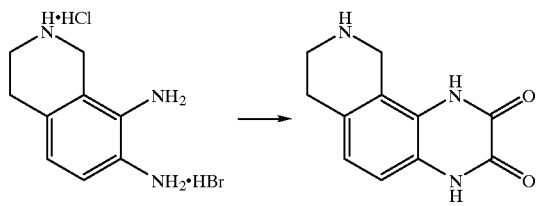

A solution of Example 29 (01.27 g, 0.96 mmol) in 25 mL 3 N HCl, was treated with oxalic acid (0.15 g, 1.2 mmol) and heated at reflux for 4 h. The mixture was cooled in an ice bath and the precipitate collected by filtration and washed with 3 N HCl, water and then diethyl ether consecutively. After air drying, the solid was suspended in 10 mL water and heated at approximately 90° C., basifyed with ammonium hydroxide solution to pH 8, and filtered hot. The solid was washed first with water, then with diethyl ether and then dried in a vacuum oven to give an off-white solid (0.17 g, 81% yield) mp=294–297° C. MS (CI) M+1, 218; IR 1691, 1659 cm$^{-1}$.

EXAMPLE 31

1,4,7,8,9,10-Hexahydro-6-nitropyrido[3,4-f]quinoxaline-2,3-dione

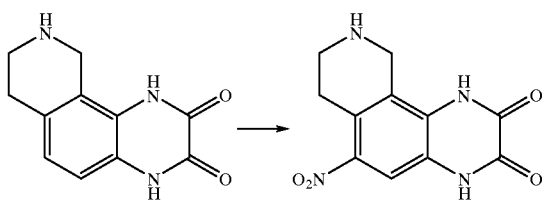

A solution of the quinoxalinedione from Example 30 (50 mg, 0.23 mmol) in 2 mL of trifluoroacetic acid was treated with fuming nitric acid (0.1 mL, 2.3 mmol) and stirred under a nitrogen atmosphere for 19 h. After evaporating to dryness, the residue was triturated with acetone and the precipitant collected by filtration. The solid was suspended in water, heated on a hot plate and basified to pH 8 with an ammonium hydroxide solution. The solid was collected by filtration while hot, and dried in vacuo to give a yellow solid (35 mg, 65% yield). mp=245–240° C. CHN calc'd for $C_{11}H_{10}N_4O_4$ found within theoretical limit ±0.4.

EXAMPLE 32

1,1-dimethylethyl 4-[(1,2,3,4,7,8,9,10-octahydro-2,3-dioxopyrido[3,4-f]quinoxaline-9-yl)carbonyl]-1-piperidine carboxylate

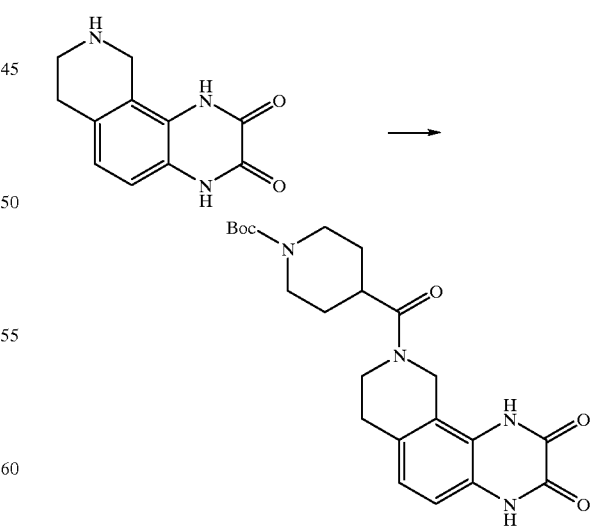

A solution of N-Boc-4-piperidinecarboxylic acid (158 mg, 0.69 mmol) and carbonyldiimidazole (119 mg, 0.69 mmol) in tetrahydrofuran (3 mL) under a nitrogen atmosphere was reluxed for 15 min. This solution was then added to suspension of the quinoxalinedione from Example 30 (100 mg, 0.46 mmol) in anhydrous dimethylformamide (3 mL). After stirring for 15 min (nitrogen atmosphere), triethylamine (0.96 mL, 0.69 mmol) was added and the reaction was stirred at 70° C. for 19 h. The mixture was concentrated to dryness and the residue triturated with water and collected by filtration. A beige solid (143 mg, 73% yield) was obtained. mp=283–286° C. CHN calc'd for $C_{22}H_{28}N_4O_5$ within ±0.4.

EXAMPLE 33

1,4,7,8,9,10-Hexahydro-9-(4-piperidinyl carbonyl)pyrido[3,4-f]quinoxaline-2,3-dione

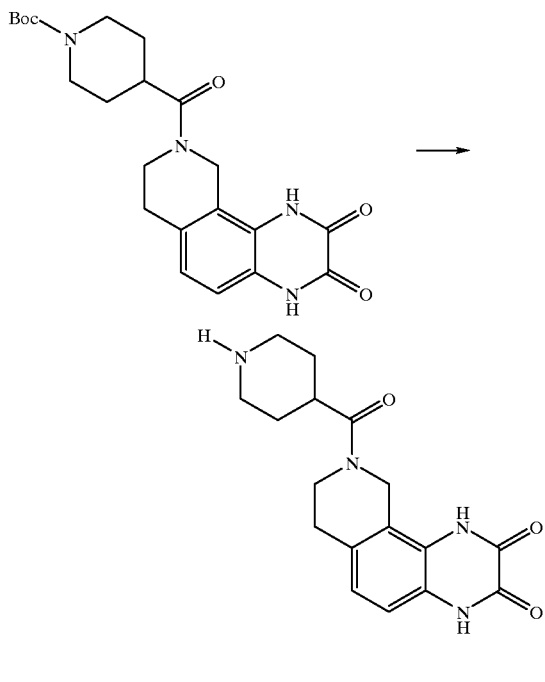

A mixture of the N-Boc quinoxalinedione from Example 32 (18 mg, 0.042 mmol) in trifluoroacetic acid (1.5 mL) was stirred under a nitrogen atmosphere for 15 min. After concentrating to dryness, the residue was triturated with water, basified to pH 8 and filtered. The filtrate was evaporated to give a beige solid (14 mg, 99% yield).

EXAMPLE 34

1,1-dimethylethyl 4-[(1,2,3,4,7,8,9,10-octahydro-6-nitro-2,3-dioxopyrido[3,4-f]quinoxaline-9-yl)carbonyl]-1-piperidine carboxylate

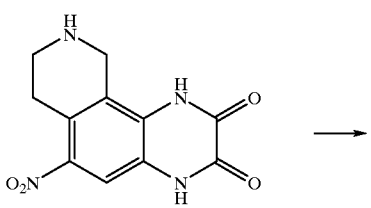

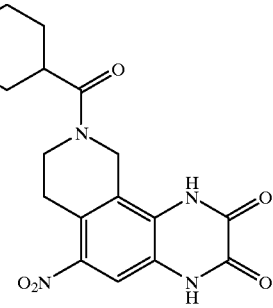

A procedure similar to that used for Example 32 was used except the 7-nitroquinoxalinedione from Example 31 (0.1 g, 0.38 mmol) was used as a reactant to give a beige solid (175 mg, 97% yield). mp=295–298° C. IR (KBr) 1715, 1704, 1648, 1536, 1342 cm$^{-1}$.

EXAMPLE 35

9-Benzoyl-1,4,7,8,9,10-hexahydro-6-nitrogyrido[3,4-f]quinoxaline-2,3-dione

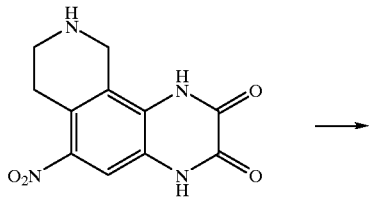

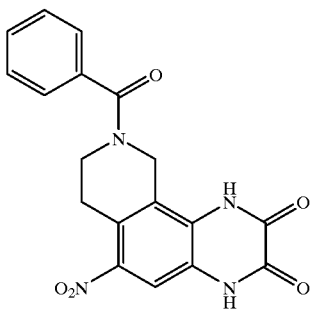

The 7-nitroquinoxalinedione from Example 31 (0.1 g, 0.38 mmol) was treated with the CDI adduct of benzoic acid (0.57 mmol) by a procedure similar to that in Example 32 to give a yellow solid (121 mg, 86% yield). mp=240–244° C. MS(CI) M+1 367; IR (KBr) 1701, 1632, 1533, 1333 cm$^{-1}$.

EXAMPLE 36

9-(Cyclohexylcarbonyl)-1,4,7,8,9,10-hexahydro-6-nitropyrido[3,4-f]quinoxaline-2,3-dione

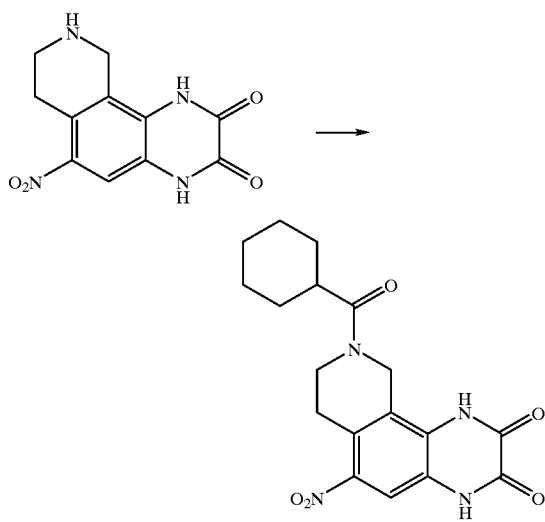

The 7-nitroquinoxalinedione from Example 31 (100 mg, 0.38 mmol) was treated with CDI adduct of cyclohexanecarboxylic acid (0.57 mmol) by a procedure similar to that in Example 32 to give a beige solid (100 mg, 70% yield). mp,300° C. MS(CI) M+1 373; IR (KBr) 1705, 1645, 1537, 1346 cm$^{-1}$.

EXAMPLE 37

9-(4-Chlorobenzoyl)-1,4,7,8,9,10-hexahydro-6-nitropyrido[3,4-f]quinoxaline-2,3-dione

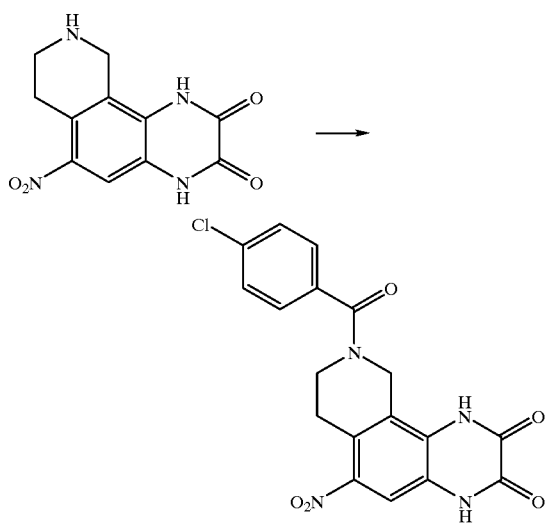

The 7-nitroquinoxalinedione from Example 31 (100 mg, 0.38 mmol) was treated with the CDI adduct of 4-chlorobenzoic acid (0.57 mmol) by a procedure similar to that in Example 32 to give a yellow solid (159 mg, 99% yield). mp=280–283° C. (dec.). MS(CI) M+1 401; CHN calc'd for $C_{18}H_{13}ClN_4O_5$ within ±0.4.

EXAMPLE 38

1,4,7,8,9,10-Hexahydro-6-nitro-9-(phenylacetyl)pyrido[3,4-f]quinoxaline-2,3-dione

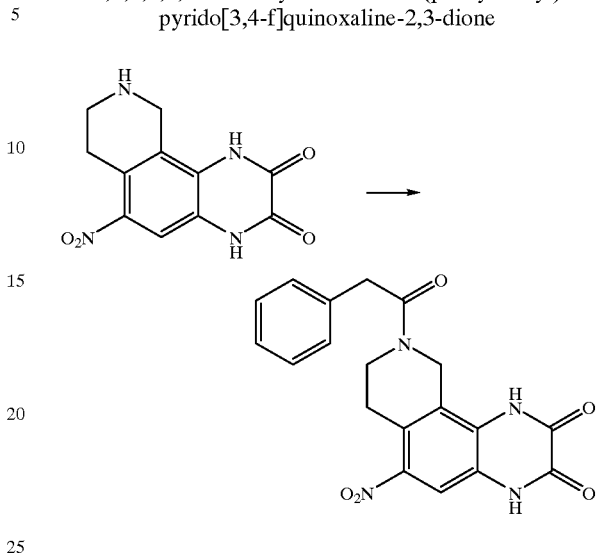

The 7-nitroquinoxalinedione from Example 31 (100 mg, 0.38 mmol) was treated with the CDI adduct of phenylacetic acid (0.57 mmol) by a procedure similar to that in Example 32 to give a beige solid (123 mg). MS(CI) M+1 381; IR (KBr) 1710, 1638, 1535, 1339 cm$^{-1}$.

EXAMPLE 39

9-[(4-chlorophenyl)acetyl]-1,4,7,8,9,10-hexahydro-6-nitropyrido[3,4-f]quinoxaline-2,3-dione

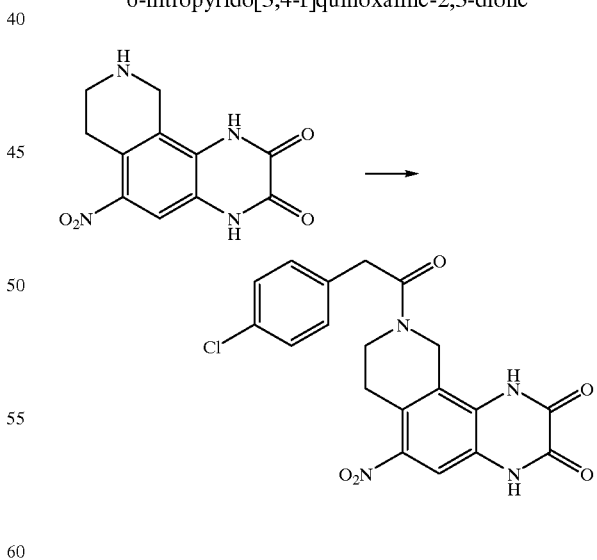

The 7-nitroquinoxalinedione from Example 31 (100 mg, 0.38 mmol) was treated with the CDI adduct of (4-chlorophenyl)acetic acid (0.57 mmol) by a procedure similar to that in Example 32 to give a yellow solid (156 mg). MS(CI) M+1 415; IR (KBr) 1755, 1734, 1556, 1376 cm$^{-1}$.

EXAMPLE 40

8-Bromo-1,2,3,4-tetrahydro-6-nitro-2-(phenylmethyl)-5-isoquinolinamine

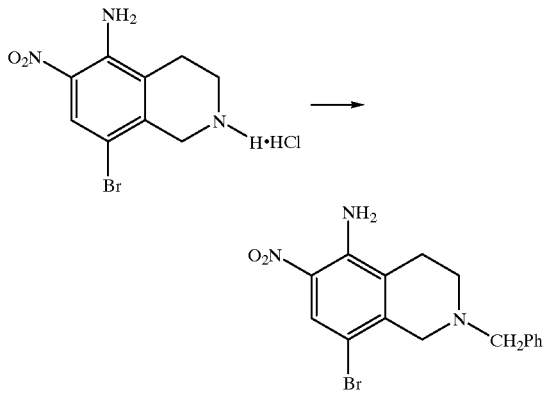

A solution of benzaldehyde (0.66 mL, 6.47 mmol) and the product from Example 23 (1 g, 3.24 mmol) in 30 mL 2:1 methanol:water was treated with sodium cyanoborohydride (~0.61 g, 9.7 mmol) at room temperature. After 1 h, additional benzaldehyde (0.5 mL) and sodium cyanoborohydride (0.5 g) were added and stirred for 30 min. The reaction mixture was quenched with saturated aqueous sodium bicarbonate, the aqueous layer extracted with chloroform and evaporated after drying over magnesium sulfate to give 1.05 g.

EXAMPLE 41

8-Bromo-1,2,3,4-tetrahydro-2-(phenylmethyl)-5,6-isoquinolinediamine

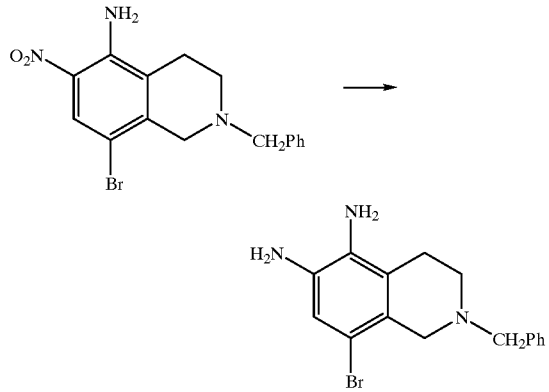

A solution of the product from Example 40 (0.66 g, 1.82 mmol) in 50 mL tetrahydrofuran was hydrogenated over Raney nickel for 3 h. The catalyst was removed by filtration, and the filtrate concentrated to give the diamine as a brown oil. This was used without further purification.

EXAMPLE 42

6-Bromo-1,4,7,8,9,10-hexahydro-8-(phenylmethyl)pyrido[3,4-f]quinoxaline-2,3-dione hydrochloride

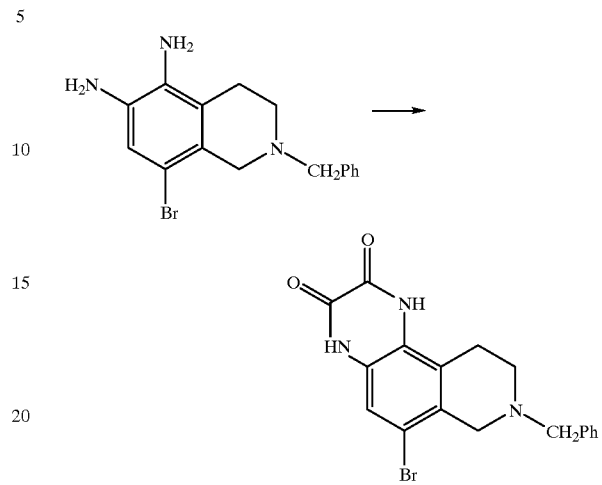

A suspension of the diamine from Example 41 (1.82 mmol) nd oxalic acid dihydrate (0.34 g) in 15 mL 3 N HCl was heated at reflux for 4 h. After cooling to 0° C., the precipitate was collected by filtration and washed with water. The residue was dried in vacuo at 100° C. over phosphorous pentoxide to give a pink solid (0.47) g). C,H,N. calc'd C, 49.05; found C,49.64.

EXAMPLE 43

8-Bromo-1,2,3,4-tetrahydro-6-nitro-2-(2-phenylethyl)-5-isoquinolinamine

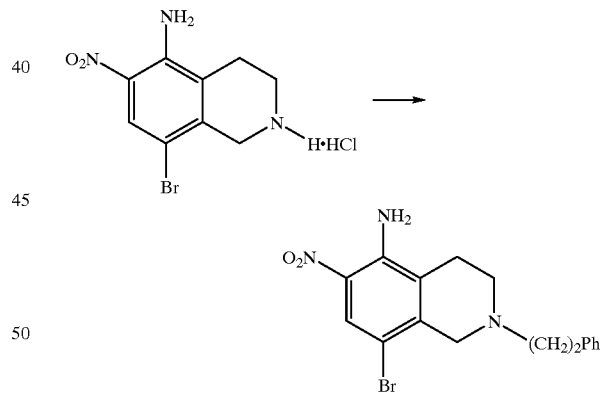

A solution of phenylacetaldehyde (1.0 mL) and the product from Example 23 (1.5 g, 4.86 mmol) in 45 mL 2:1 methanol:water was treated with excess sodium cyanoborohydride at room temperature. After 1 h, additional phenylacetaldehyde (0.5 mL) and sodium cyanoborohydride (0.5 g) were added and stirred for 30 min. The reaction mixture was quenched with saturated aqueous sodium bicarbonate and the aqueous layer was extracted with chloroform. The chloroform extract was evaporated after drying over magnesium sulfate. The residue was purified by silica gel column chromatography (4:1 chloroform:ethyl acetate as eluant). The resulting red solid was suspended in hexane, collected by filtration and dried in vacuo (1.17 g, 62% yield).

EXAMPLE 44

8-Bromo-1,2,3,4-tetrahydro-2-(2-phenylethyl)-5,6-isoquinolinediamine

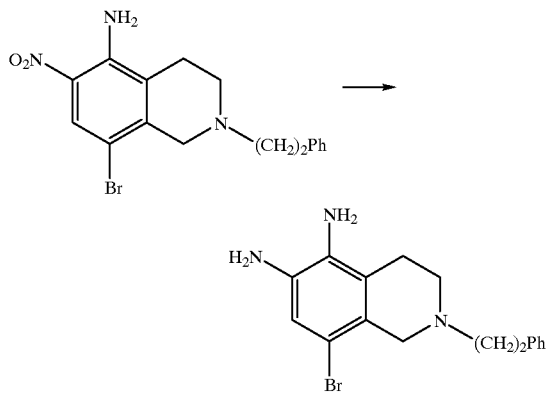

A solution of the product from Example 43 (0.6 g, 1.6 mmol) in 50 mL tetrahydrofuran was hydrogenated over Raney nickel (0.4 g) until no starting material remained. The catalyst was removed by filtration, the filtrate evaporated to give the diamine as an oil. This was used directly with no further purification.

EXAMPLE 45

6-Bromo-1,4,7,8,9,10-hexahydro-8-(2-phenylethyl)pyrido[3,4-f]quinoxaline-2,3-dione hydrochloride

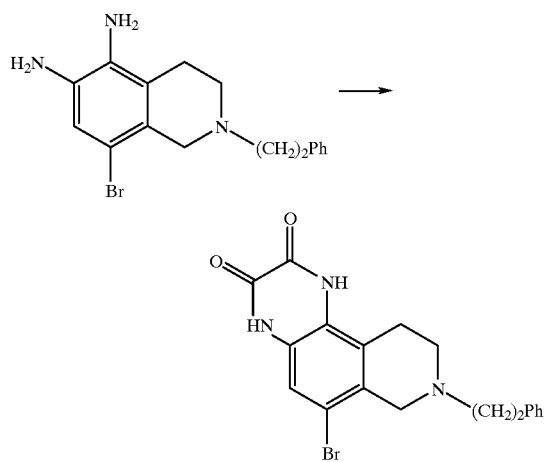

The diamine from Example 44 (1.6 mmol) and oxalic acid dihydrate in 10 mL of 3 N HCl was heated at 100° C. for 4 h. The resulting pink solid was collected by filtration.

EXAMPLE 46

8-Bromo-1,2,3,4-tetrahydro-6-nitro-2-[[3-(trifluoromethyl)phenyl]methyl]-5-isoquinolinamine

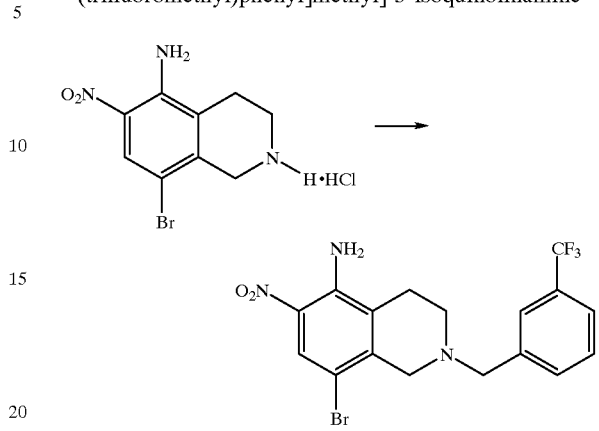

A solution of 3-trifluoromethylbenzaldehyde (1.69 g, 9.72 mmol) and the product from Example 23 (1.5 g, 4.86 mmol) in 45 mL 2:1 methanol:water was treated with sodium cyanoborohydride (0.92 g) at room temperature. After 1 h, additional trifluoromethylbenzaldehyde (0.5 mL) and sodium cyanoborohydride (0.5 g) were added and stirred for 30 min. The reaction mixture was quenched with saturated aqueous sodium bicarbonate and the aqueous layer was extracted with chloroform. The chloroform extract was evaporated after drying over magnesium sulfate. The residue was purified by silica gel column chromatography (1:1 chloroform:ethyl acetate as eluant). The resulting yellow solid was suspended in hexane, collected by filtration and dried in vacuo (1.62 g).

EXAMPLE 47

8-Bromo-1,2,3,4-tetrahydro-2-[[4-(trifluoromethyl)phenyl]methyl]-5,6-isoquinolinediamine

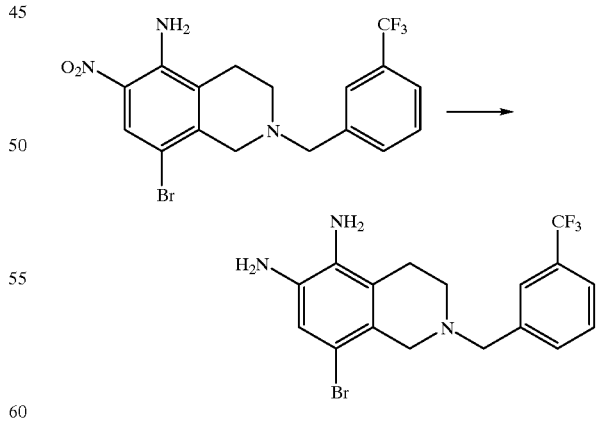

The product from Example 46 (0.7 g, 1.63 mmol) in 50 mL tetrahydrofuran was hydrogenated over Raney nickel (1 g) for 2 h. After removing the catalyst by filtration, the filtrate was concentrated to give the diamine, which was used directly without further purification.

EXAMPLE 48

6-Bromo-1,4,7,8,9,10-Hexahydro-8-[[4-(trifluoromethyl)methyl]pyrido[3,4-f]quinoxaline-2,3-dione hydrochloride

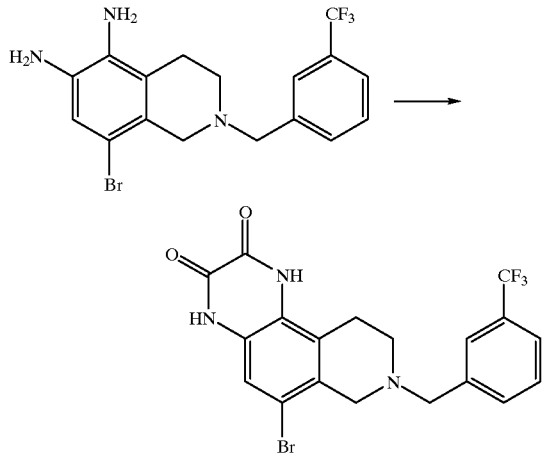

The diamine from Example 47 (1.63 mmol) and oxalic acid dihydrate (0.41 g) was refluxed in 20 mL 3 N HCl for 4 h. After cooling the solid residue was collected by filtration and washed with water, and then with ethanol. The light blue solid was dried at 100° C. in vacuo (0.54 g).

C,H,N,Cl cal'd for: C, 44.86; Cl, 6.97; found C, 45.29; Cl, 5.38.

EXAMPLE 49

8-Bromo-1,2,3,4-tetrahydro-6-nitro-2-[(3-chlorophenyl)methyl]-5-isoquinolinamine

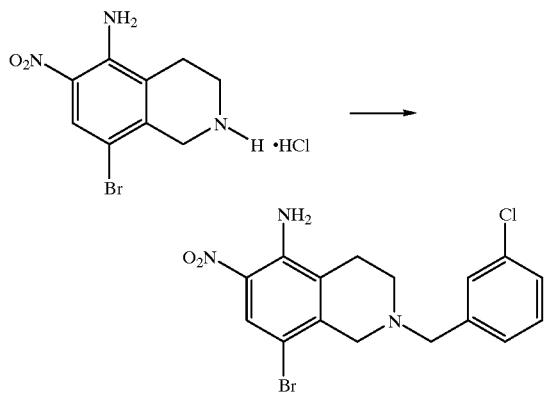

A solution of 3-chlorobenzaldehyde (1.1 mL, 9.72 mmol) and the product from Example 23 (1.5 g 4.86 mmol) in 45 mL 2:1 methanol:water was treated with sodium cyanoborohydride (0.92 9, 14.6 mmol) at room temperature. After 1 h, additional phenylacetaldehyde (0.5 mL) and sodium cyanoborohydride (0.5 g) were added and stirred for 30 min. The reaction mixture was quenched with saturated aqueous sodium bicarbonate and the aqueous layer was extracted with chloroform. The chloroform extract was evaporated after drying over magnesium sulfate. The residue was purified by silica gel column chromatography (4:1 chloroform:ethyl acetate as eluant). The resulting yellow solid was suspended in hexane, collected by filtration and dried in vacuo (0.63 g).

EXAMPLE 50

8-Bromo-1,2,3,4-tetrahydro-2-[(3-chlorophenyl)methyl]-5,6-isoquinolinediamine

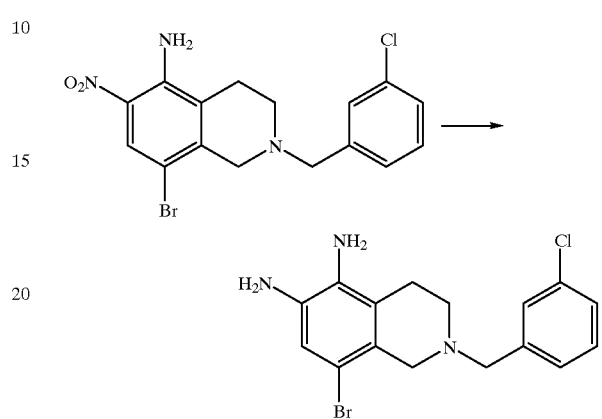

The product from Example 49 (0.58 g, 1.47 mmol) in 50 mL tetrahydrofuran was hydrogenated over Raney nickel (1 m) for 2 h. After removing the catalyst by filtration, the filtrate was concentrated to give the diamine, which was used directly without further purification.

EXAMPLE 51

6-Bromo-1,4,7,8,9,10-hexahydro-8-[(3-chlorophenyl)methyl]pyrido[3,4-f]quinoxaline-2,3-dione hydrochloride

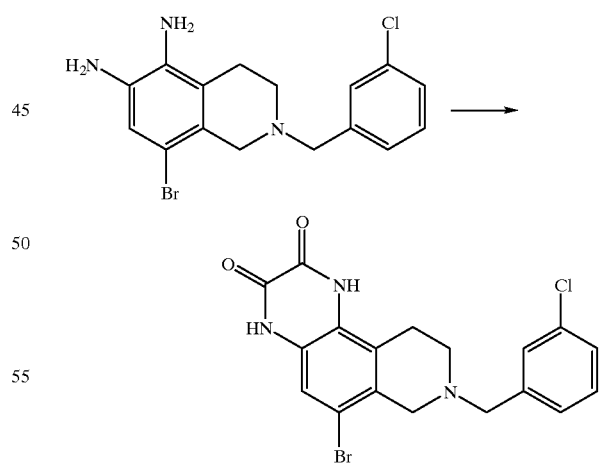

The diamine from Example 50 (1.47 mmol) and oxalic acid dihydrate (0.37 g, 2.93 mmol) in 20 mL 3 N HCl was degassed (in vacuo and nitrogen) and heated at reflux for 4 h. After cooling to room temperature, the solid was collected by filtration, washed with ethanol, and dried in vacuo at 100° C. to give a blue solid (0.47 g).

EXAMPLE 52

8-Bromo-1,2,3,4-tetrahydro-6-nitro-2-[3-phenylpropyl]-5-isoquinolinamine

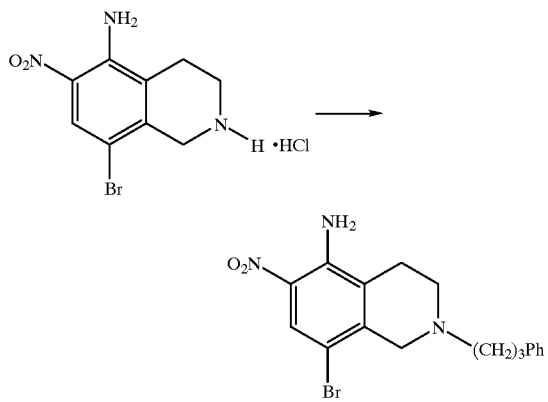

A solution of phenylpropioaldehyde (0.9 mL, 6.47 mmol) and the product from Example 23 (1.0 g, 3.24 mmol) in 30 mL 2:1 methanol:water was treated with excess sodium cyanoborohydride at room temperature. After 1 h, additional phenylpropioaldehyde (0.5 mL) and sodium cyanoborohydride (0.5 g) were added and stirred for 30 min. The reaction mixture was quenched with saturate aqueous sodium bicarbonate and the aqueous layer extracted with chloroform. The chloroform extract was evaporated after drying over magnesium sulfate. The residue was purified by silica gel column chromatography (4:1 chloroform:ethyl acetate as eluant). The resulting solid was suspended in hexane, collected by filtration and dried in vacuo (1.22 g, 96% yield).

EXAMPLE 53

8-Bromo-1,2,3,4-tetrahydro-2-[3-phenylpropyl]-5,6-isoquinolinediamine

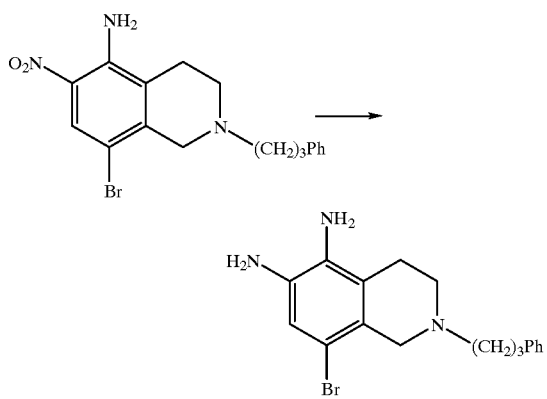

The product from Example 52 (0.50 g, 1.28 mmol) in 50 mL tetrahydrofuran was hydrogenated over Raney nickel (1 g) for 2 h. After removing the catalyst by filtration, the filtrate was concentrated to give the diamine, which was used directly without further purification.

EXAMPLE 54

6-Bromo-1,4,7,8,9,10-hexahydro-8-(3-phenylpropyl)pyrido[3,4-f]quinoxaline-2,3-dione hydrochloride

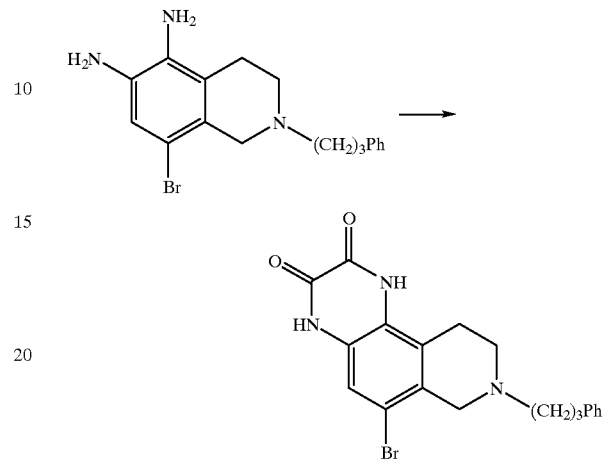

The diamine from Example 49 (1.28 mmol) and oxalic acid dihydrate (0.325 g, 2.56 mmol) in 20 mL 3 N HCl was degassed (in vacuo and nitrogen) and heated at reflux for 4 h. After cooling to room temperature, the solid was collected by filtration, washed with ethanol, then diethyl ether, and subsequently dried in vacuo at 100° C. to give a pink solid (0.385 g). C,H,N,Cl cal'd for: C, 53.29; Cl, 7.86; found C, 53.75; Cl, 6.85.

What is claimed is:

1. A nitrogen substituted azacycloalkyl ring fused 2,3 quinoxalinedione compound represented by the formula:

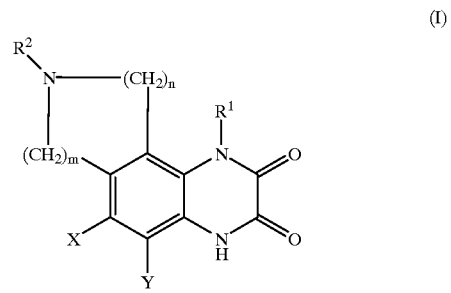

(I)

or a pharmaceutically acceptable salt thereof wherein $R^1$ is hydrogen, alkyl or W-alkyl;

X and Y are independently hydrogen, halogen, nitro, cyano, trifluoromethyl, $SO_2CF_3$, $SO_2R^4$, $SO_2NR^4R^5$, alkyl, alkenyl, $(CH_2)_zCONR^4R^5$, $(CH_2)_zCOOR^4$, or $NHCOR^4$, wherein $R^4$ and $R^5$ are independently hydrogen, alkyl having 1 to 6 carbon atoms, cycloalkyl or W-alkyl, and z is an integer from 0 to 4;

$R^2$ is benzoyl, W, W-alkyl, COcycloalkyl, COalkyl-W, $CONR^3$alkyl, $CONR^3$-W, $CONR^3$alkyl-W, $CSNR^3$alkyl, $CSNR^3$alkyl-W,

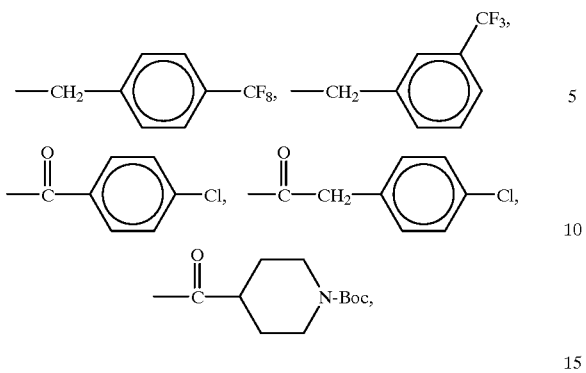

or a moiety derived from a common amino acid by removal of the —OH from the carboxyl group which is alpha to the amino, wherein $R^3$ is hydrogen, alkyl or W-alkyl and wherein W is phenyl, naphthyl, thienyl, furyl, tetrazolyl, pyrrolyl, pyrimidinyl, triazolyl, imidazolyl, piperidyl, piperazinyl, morpholinyl or pyrrolinyl;

and m and n are independently 0, 1 or 2 provided that m+n is >1;

provided that when $R^2$ is benzoyl,

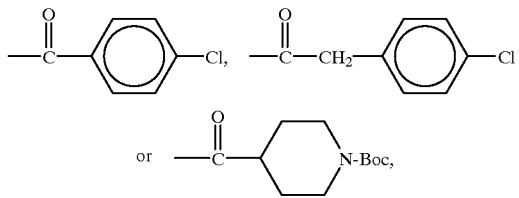

X is nitro, Y and $R^1$ are H, m is 2 and n is 1; where $R^2$ is

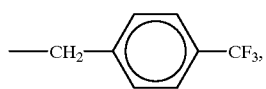

X is nitro, Y and $R^1$ are H, and m is 2 and n is 1; or when $R^2$ is

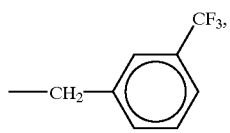

X is bromo, Y and $R^1$ are H, m is 1 and n is 2.

2. A compound according to claim 1, wherein the azacycloalkyl ring is a six membered ring and either (i) m is 1 and n is 2 or (ii) m is 2 and n is 1.

3. A compound according to claim 2, wherein Y is hydrogen.

4. A compound according to claim 1, wherein X is hydrogen, bromo or nitro.

5. A compound according to claim 1, wherein X is nitro.

6. A compound according to claim 1, wherein $R^2$ is

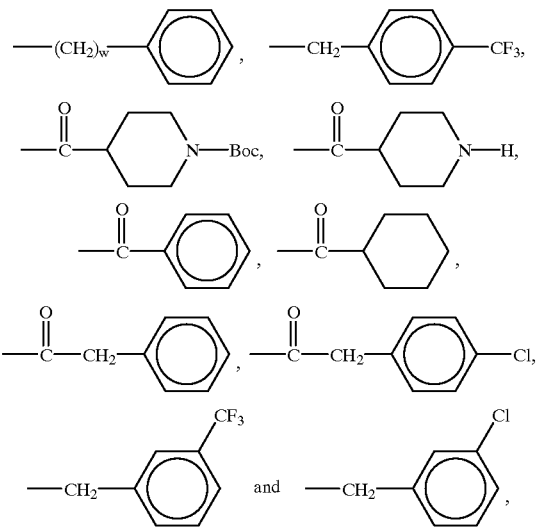

wherein w is 1–3.

7. A compound selected from the group consisting of:
6-Bromo-1,4,7,8,9,10-hexahydro-9-(phenylmethyl) pyrido[3,4-f]quinoxaline-2,3-dione,
6-Bromo-1,4,7,8,9,10-hexahydro-9-(2-phenylethyl) pyrido[3,4-f]quinoxaline-2,3-dione,
6-Bromo-1,4,7,8,9,10-hexahydro-9-(3-phenylpropyl) pyrido[3,4 -f]quinoxaline-2,3-dione,
1,4,7,8,9,10-Hexahydro-9-[[3-(trifluoromethyl)phenyl] methyl]pyrido[3,4-f]quinoxaline-2,3-dione,
1,4,7,8,9,10-Hexahydro-6-nitro-9-[[4-trifluoromethyl) phenyl]methyl]pyrido[3,4-f]quinoxaline-2,3-dione,
1,4,7,8,9,10-Hexahydro-9-[[4-trifluoromethyl)phenyl] methyl]pyrido[3,4-f]quinoxaline-2,3-dione methanesulfonate (1:1) salt,
1,4,7,8,9,10-Hexahydro-8-[[4-trifluoromethyl)phenyl] methyl]pyrido[4,3-f]quinoxaline-2,3-dione,
1,4,7,8,9,10 Hexahydro-6-nitro-8-[[4-(trifluoromethyl) phenyl]methyl]pyrido[4,3-f]quinoxaline-2,3-dione,
1,4,7,8,9,10-Hexahydro-6-nitro-8-[[4-(trifluoromethyl) phenyl]methyl]pyrido[4,3-f]quinoxaline-2,3-dione methanesulfonate (1:1)salt,
1,1-dimethylethyl 4-[(1,2,3,4,7,8,9,10-octahydro-2,3-dioxopyrido[3,4-f]quinoxaline-9-yl)carbony]-1-piperidine carboxylate,
1,4,7,8,9,10-Hexahydro-9-(4-piperidinylcarbonyl)pyrido [3,4-f]quinoxaline-2,3-dione,
1,1-dimethylethyl 4-[(1,2,3,4,7,8,9,10-octahydro-6-nitro-2,3-dioxopyrido[3,4-f]quinoxaline-9-yl)carbonyl]-1-piperidine carboxylate,
9-Benzoyl-1,4,7,8,9,10-hexahydro-6-nitropyrido[3,4-f] quinoxaline-2,3-dione,
9-(Cyclohexylcarbonyl)-1,4,7,8,9,10-hexahydro-6-nitropyrido[3,4-f]quinoxaline-2,3-dione,
9-(4-Chlorobenzoyl)-1,4,7,8,9,10-hexahydro-6-nitropyrido[3,4-f]quinoxaline-2,3-dione,
1,4,7,8,9,10-Hexahydro-6-nitro-9-(phenylacetyl)pyrido [3,4-f]quinoxaline-2,3-dione,
9-[(4-chlorophenyl)acetyl]-1,4,7,8,9,10-hexahydro-6-nitropyrido(3,4-f]quinoxaline-2,3-dione, 6-Bromo-1,4,7,8,9,10-hexahydro-8-(phenylmethyl)pyrido[3,4-f]quinoxaline-2,3-dione hydrochloride, 6-Bromo-1,4,7,8,9,10-hexahydro-8-(2-phenylethyl)pyrido[3,4-f]quinoxaline-2,3-dione hydrochloride, 6-Bromo-1,4,7,8,9,10-Hexahydro-8-[[4-(trifluoromethyl)methyl]pyrido[3,4-f]quinoxaline-2,3-dione hydrochloride, 6-Bromo-1,4,7,8,9,10-hexahydro-8-[(3-chlorophenyl)methyl]pyrido[3,4-f]quinoxaline-2,3-dione hydrochloride and 6-Bromo-1,4,7,8,9,10-hexahydro-8-(3-phenylpropyl)pyrido[3,4-f]quinoxaline-2,3-dione hydrochloride.

8. A pharmaceutical composition for treating disorders selected from the group consisting of epilepsy, schizophrenia, neuropathic pain, central nervous systems degenerative disorders, cerebral hypoxia/ischemic conditions, said composition comprising a pharmaceutically acceptable carrier or diluent and a therapeutically effective amount of at least one compound of claim 1.

9. A method for treating epilepsy which comprises administering at least one compound of claim 1 in unit dosage form.

10. A method for treating cerebral hypoxic/ischemia which comprises administering at least one compound of claim 1 in unit dosage form.

* * * * *

UNITED STATES PATENT AND TRADEMARK OFFICE
CERTIFICATE OF CORRECTION

PATENT NO. : 6,057,313
APPLICATION NO. : 08/869515
DATED : May 2, 2000
INVENTOR(S) : Christopher Franklin Bigge et al.

It is certified that error appears in the above-identified patent and that said Letters Patent is hereby corrected as shown below:

COLUMN 4

Line 18, "$SO_2R^4$" should read --$SO_2R^4$;--; and
Line 23, "W-alkylCOOR$^3$," should read --$R^2$ is alkylCOOR$^3$, and "W-aryl;" should read --W, W-alkyl,--.

COLUMN 5

Line 35, " 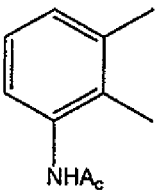 " should read -- 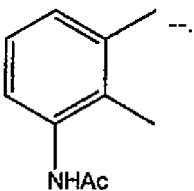 --.

COLUMN 7

Line 14, "  " should read --  --;

Line 20, " 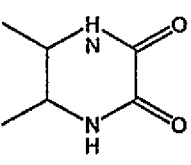 " should read -- 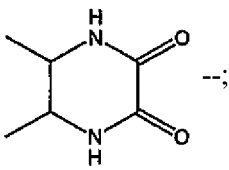 --;

Line 27, "electrophillic" should read --electrophilic--;

Line 35, " 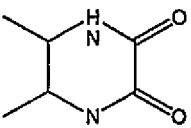 " should read -- 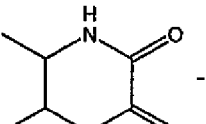 --; and

Line 60, " 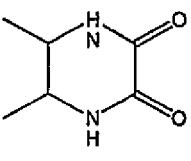 " should read -- 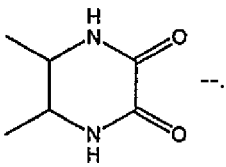 --.

UNITED STATES PATENT AND TRADEMARK OFFICE
CERTIFICATE OF CORRECTION

PATENT NO.       : 6,057,313
APPLICATION NO.  : 08/869515
DATED            : May 2, 2000
INVENTOR(S)      : Christopher Franklin Bigge et al.

It is certified that error appears in the above-identified patent and that said Letters Patent is hereby corrected as shown below:

COLUMN 8

Line 3, "electrophillic" should read --electrophilic--;

Line 10, " 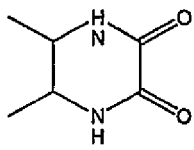 " should read -- 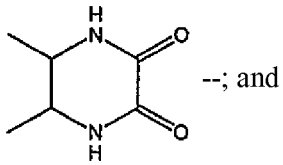 --; and

Line 33, "Exemplarary" should read --Exemplary--.

COLUMN 9

Line 5, " 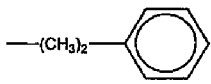 " should read -- 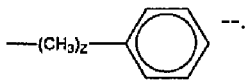 --;

Line 19, "alkylquanidine," should read --alkylguanidine,--; and

Line 49, "  " should read --  --.

COLUMN 10

Line 31, "2,3-dione" should read --2,3-dione;--.

COLUMN 12

Line 3, "Schemes T" should read --Schemes I--; and
Line 10, "schemes II" should read --Schemes II--.

UNITED STATES PATENT AND TRADEMARK OFFICE
CERTIFICATE OF CORRECTION

PATENT NO.         : 6,057,313
APPLICATION NO. : 08/869515
DATED                  : May 2, 2000
INVENTOR(S)        : Christopher Franklin Bigge et al.

It is certified that error appears in the above-identified patent and that said Letters Patent is hereby corrected as shown below:

COLUMNS 11-14

Scheme II should read as follows:

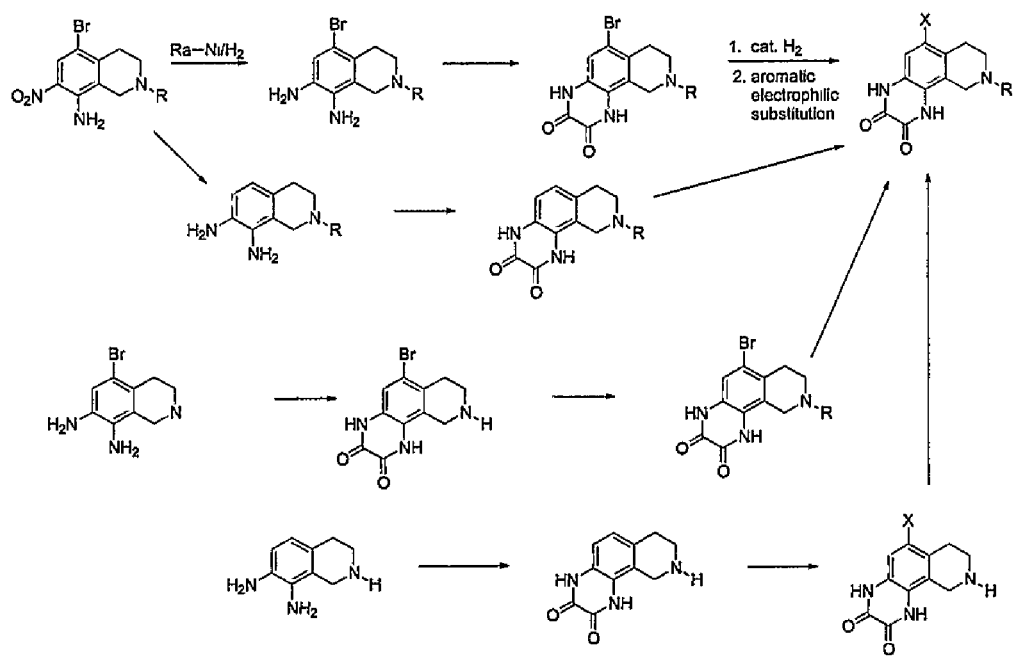

COLUMN 15

Line 47, " >N—AC " should read -- >N—Ac --; and

Line 57, " >N—AC " should read -- >N—Ac --.

COLUMN 16

Line 43, " >N—AC " should read -- >N—Ac --; and

Line 56, " >N—AC " should read -- >N—Ac --.

UNITED STATES PATENT AND TRADEMARK OFFICE
CERTIFICATE OF CORRECTION

PATENT NO. : 6,057,313
APPLICATION NO. : 08/869515
DATED : May 2, 2000
INVENTOR(S) : Christopher Franklin Bigge et al.

It is certified that error appears in the above-identified patent and that said Letters Patent is hereby corrected as shown below:

COLUMN 18

Line 27, "electrophillic" should read --electrophilic--.

COLUMN 19

Line 3, "electrophillic" should read --electrophilic--;
Line 19, "$R^{20}$ CHO" should read --$R^{2'}$CHO--; and
Line 27, "herein," should read --herein--.

COLUMN 20

Line 55, "Ouinoxalinediones" should read --Quinoxalinediones--; and
Line 61, "$\frac{100}{100}$" should read --$\frac{>100}{>100}$--.

COLUMN 21

Line 4, "Ouinoxalinediones" should read --Quinoxalinediones--;
Line 22, "19:409-428." should read --19:409-428).--; and
Line 36, "comprises" should read --comprise--.

COLUMN 22

Line 19, "basifyied" should read --basified--; and
Line 47, "(33W" should read --(33%--.

COLUMN 23

Line 35, "basifyied" should read --basified--.

COLUMN 25

Line 25, "cool" should read --cooled--; and
Line 28, "basifyed" should read --basified--.

UNITED STATES PATENT AND TRADEMARK OFFICE
CERTIFICATE OF CORRECTION

PATENT NO. : 6,057,313
APPLICATION NO. : 08/869515
DATED : May 2, 2000
INVENTOR(S) : Christopher Franklin Bigge et al.

It is certified that error appears in the above-identified patent and that said Letters Patent is hereby corrected as shown below:

COLUMN 26

Line 20, "(0.54" should read --(0.54g,--;
Line 21, "y" should read --g--;
Line 41, "(0.3" should read --(0.3g,--;
Line 42, "b," should read --g--; and "cool" should read --cooled--; and
Line 44, "basifyed" should read --basified--.

COLUMN 27

Line 58, "cool" should read --cooled--.

COLUMN 28

Line 2, "basifyed" should read --basified--.

COLUMN 30

Line 42, "acetamiade" should read --acetamide--.

COLUMN 33

Line 22, "(100 mL" should read --(100 mL)--;
Line 63, "cool" should read --cooled--; and
Line 65, "basifyed" should read --basified--.

COLUMN 36

Line 4 "basifyed" should read --basified--.

COLUMN 37

Line 1, "reluxed" should read --refluxed--.

COLUMN 38

Line 31, "-6-nitrogyrido[3," should read -- -6-nitropyrido[3,--.

COLUMN 39

Line 31, "mp,300° C." should read --mp > 300° C.--.

UNITED STATES PATENT AND TRADEMARK OFFICE
CERTIFICATE OF CORRECTION

PATENT NO. : 6,057,313  
APPLICATION NO. : 08/869515  
DATED : May 2, 2000  
INVENTOR(S) : Christopher Franklin Bigge et al.

Page 6 of 7

It is certified that error appears in the above-identified patent and that said Letters Patent is hereby corrected as shown below:

COLUMN 42

Line 26, "nd" should read --and--; and
Line 30, "(0.47)g)." should read --(0.47g).--.

COLUMN 44

Line 42, "[[4-(trifluoromethyl)" should read --[[3-(trifluoromethyl)--.

COLUMN 45

Line 3, "[[4-" should read --[[3- --;
Line 57, "(1.5g" should read --(1.5g,--; and
Line 59, "(0.92 9," should read --(0.92g,--.

COLUMN 46

Line 29, "(1" should read --(1g)--;
Line 30, "m)" should read --g)--.

COLUMN 49

Line 5, " 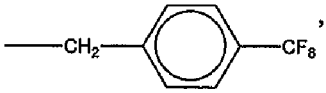 , " should read --  , --.

COLUMN 50

Line 66, "(3,4-f]" should read --[3,4-f]--.

UNITED STATES PATENT AND TRADEMARK OFFICE
CERTIFICATE OF CORRECTION

| | |
|---|---|
| PATENT NO. | : 6,057,313 |
| APPLICATION NO. | : 08/869515 |
| DATED | : May 2, 2000 |
| INVENTOR(S) | : Christopher Franklin Bigge et al. |

It is certified that error appears in the above-identified patent and that said Letters Patent is hereby corrected as shown below:

COLUMN 52

Line 10, "hypoxic/ischemia" should read --hypoxia/ischemia--.

Signed and Sealed this

Eleventh Day of September, 2007

JON W. DUDAS
*Director of the United States Patent and Trademark Office*